US010087224B2

(12) United States Patent
Zhou et al.

(10) Patent No.: US 10,087,224 B2
(45) Date of Patent: Oct. 2, 2018

(54) GENE THERAPY FOR ALZHEIMER'S AND OTHER NEURODEGENERATIVE DISEASES AND CONDITIONS

(71) Applicant: CORNELL UNIVERSITY, Ithaca, NY (US)

(72) Inventors: Ping Zhou, Fresh Meadows, NY (US); Costantino Iadecola, New York, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 14/530,049

(22) Filed: Oct. 31, 2014

(65) Prior Publication Data

US 2015/0126590 A1 May 7, 2015

Related U.S. Application Data

(60) Provisional application No. 61/898,776, filed on Nov. 1, 2013.

(51) Int. Cl.
*C07K 14/47* (2006.01)

(52) U.S. Cl.
CPC ........... *C07K 14/4702* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | | |
|---|---|---|---|
| 4,797,368 A | 1/1989 | Carter et al. | |
| 4,863,457 A | 9/1989 | Lee | |
| 5,378,475 A | 1/1995 | Smith et al. | |
| 5,443,505 A | 8/1995 | Wong et al. | |
| 5,464,758 A | 11/1995 | Gossen et al. | |
| 5,814,618 A | 9/1998 | Bujard et al. | |
| 6,342,390 B1 | 1/2002 | Wiener et al. | |
| 6,723,551 B2 | 4/2004 | Kotin et al. | |
| 6,821,511 B2 | 11/2004 | Kotin et al. | |
| 7,112,715 B2 | 9/2006 | Chambon et al. | |
| 2017/0029464 A1* | 2/2017 | Korbelin | C07K 14/005 |

OTHER PUBLICATIONS

Zhou, et al. (2012) "Prohibitin reduces mitochondrial free radical production and protects brain cells from different injury modalities", Journal of Neuroscience, 32(2): 583-92.*
Ferrer, et al. (2007) "Abnormal levels of prohibitin ATP synthase in the substantia nigra and frontal cortex in Parkinson's disease", Neuroscience Letters, 415(3): 205-09.*
Bryan, et al. (2009) "Chapter 1: Transgenic Mouse Models of Alzheimer's Disease: Behavioral Testing and Considerations", Methods of Behavior Analysis in Neuroscience, 2nd Ed., Editor: Buccafusco, Published by CRC Press, Boca Raton, FL, Obtained from the NCBI Bookshelf, A service of the National Library of Medicine, NIH, pp. 1-10.*
Klunk, et al. (2004) "Imaging brain amyloid in Alzheimer's disease with Pittsburg Compound-B", Annals of Neurology, 55(3): 306-19.*
Goeddel, D.V., et al., Systems for Heterologous Gene Expression, Methods in Enzymology, (1990), vol. 185, pp. 3-7.
Duran-Gonzalez, J., et al., Amyloid β peptides modify the expression of antioxidant repair enzymes and a potassium channel in the septohippocampal system, Neurobiology of Aging, (2013), vol. 34, pp. 2071-2076.
Du, H., et al., Cycophilin D deficiency attenuates mitochondrial and neuronal perturbation and ameliorates learning and memory in Alzheimer's disease, Nature Medicine, (Oct. 2008), vol. 14, No. 10, pp. 1097-1105.
Cleary, J.P., et al., Natural oligomers of the amyloid-β protein specifically disrupt cognitive function, Nature Neuroscience, (Jan. 2005), vol. 8, No. 1, pp. 79-84.
Brookmeyer, R., et al., Forecasting the global burden of Alzheimer's disease, Alzheimer's & Dementia, (2007), vol. 3, pp. 186-191.
Bevins, R.A., et al., Object recognition in rates and mice: a one-trial non-matching-to-sample learning task tostudy 'recognition memory', Nature Protocols, (2006), vol. 1, No. 3, pp. 1306-1311.
Carter, B.J., et al., Adeno-Associated Virus Vectors in Clinical Trials, Human Gene Therapy, (May 2005), vol. 16, pp. 541-550.
Fuhrmann-Benzakein, E., et al., Inducible and irreversible control of gene expression using a single transgene, Nucleic Acids Research, (2000), vol. 28, No. 23, e99, 4 pages.
Anandatheerthavarada, H.K., et al., Mitochondrial targeting and a novel transmembrane arrest of Alzheimer's amyloid precursor protein impairs mitochondrial function in neuronal cells, The Journal of Cell Biology, (2003), vol. 161, No. 1, pp. 41-54.
Bantel-Schaal, U., et al., Human Adeno-Associated Virus Type 5 Is Only Distantly Related to Other Known Primate Helper-Dependent Parvoviruses, Journal of Virology, (Feb. 1999), vol. 73, No. 2, pp. 939-947.
Chiorini, J.A., et al., Cloning of Adeno-Associated Virus Type 4 (AAV4) and Generation of Recombinant AAV4 Particles, Journal of Virology, (Sep. 1997), vol. 71, No. 9, pp. 6823-6833.
Chiorini, J.A., et al., Cloning and Characterization of Adeno-Associated Virus Type 5, Journal of Virology, (Feb. 1999), vol. 73, No. 2, pp. 1309-1319.
Cearley, C.N., et al., Transduction Characteristics of Adeno-associated Virus Vectors Expressing Cap Serotypes 7, 8, 9, and Rh10 in the Mouse Brain, Molecular Therapy, (Mar. 2006), vol. 13, No. 3, pp. 528-537.
Daly, T.M., et al., Neonatal gene transfer leads to widespread correction of pathology in a murine model of lysosomal storage disease, Proc. Natl. Acad. Sci., (Mar. 1999), vol. 96, pp. 2296-2300.
De, B.P., et al., High Levels of Persistent Expression of α1-Antitrypsin Mediated by the Nonhuman Primate Serotype rh. 10 Adeno-associated Virus Despite Preexisting Immunity to Common Human Adeno-associated Virusus, Molecular Therapy, (Jan. 2006), vol. 13, No. 1, pp. 67-76.

(Continued)

*Primary Examiner* — Robert M Kelly
(74) *Attorney, Agent, or Firm* — Scully, Scott, Murphy & Presser, P.C.

(57) ABSTRACT

The present invention provides compositions and methods to treat Alzheimer's disease and other neurodegenerative diseases and conditions by expressing exogenous prohibitin in the neurons of the brain of the subject.

11 Claims, 8 Drawing Sheets

Specification includes a Sequence Listing.

(56) References Cited

OTHER PUBLICATIONS

Ehehalt, R., et al., Amyloidogenic processing of the Alzheimer β-amyloid precursor protein depends on lipid rafts, The Journal of Cell Biology, (2003), vol. 160, No. 1, pp. 113-123.
Gao, G., et al., Novel adeno-associated viruses from rhesus monkeys as vectors for human gene therapy, Proc. Natl. Acad. Sci., (Sep. 3, 2002), vol. 99. No. 18, pp. 11854-11859.
Gao, G. et al., Clades of Adeno-Associated Viruses Are Widely Disseminated in Human Tissues, Journal of Virology, (Jun. 2004), vol. 78, No. 12, pp. 6381-6388.
Gao, G. et al., Biology of AAV Serotype Vectors in Liver-Directed Gene Transfer to Nonhuman Primates, Molecular Therapy, (Jan. 2006), vol. 13, No. 1, pp. 77-87.
Indra, A.K., et al., Temporally-controlled site-specific mutagenesis in the basel layer of the epidermis: comparison of the recombinase activity of the tamoxifen-inducible Cre-ERT and Cre-ERT2 recombinases, Nucleic Acids Research, (1999), vol. 27, No. 22, pp. 4324-4327.
Kantor, B., et al., Clinical Applications Involving CNS Gene Transfer, Advances in Genetics, (2014), vol. 87, Chapter 2, pp. 71-124.
Kaplitt, M.G., et al., Safety and tolerability of gene therapy with an adeno-associated virus (AAV) borne GAD gene for Parkinson's disease: an open label, phase I trial, The Lancet, (Jun. 23, 2007), vol. 369, pp. 2097-2105.
Leone, P. et al., Long-Term Follow-up After Gene Therapy for Canavan Disease, Sci. Transl. Med., (Dec. 19, 2012), vol. 4, Issue 165, pp. 1-13.
Ma, T. et al., Amyloid β-Induced Impairments in Hippocampal Synaptic Plasticity Are rescued by Decreasing Mitochondrial Superoxide, The Journal of Neuroscience, (Apr. 13, 2011), vol. 31, No. 15, pp. 5589-5595.
Manczak, M. et al., Mitochondria are a direct site of Aβ accumulation in Alzheimer's disease nuerons: implications for free radical generation and oxidative damage in disease progression, Human Molecular Genetics, (2006), vol. 15, No. 9, pp. 1437-1449.
Mao, Y., et al., Persistent Suppression of Ocular Neovascularization with Intravitreal Administration of AAVrh.10 Coding for Bevacizumab, Human Gene Therapy, (Dec. 2011), vol. 22, pp. 1525-1535.
Merkwirth, C., et al., Loss of Prohibitin Membrane Scaffolds Impairs Mitochondrial Architecture and Leads to Tau Hyperphosphorylation and Neurodegeneration, PLOS Genetics, (Nov. 2012), vol. 8, Issue 11, pp. 1-13.
No, D., et al., Ecdysone-inducible gene expression in mammalian cells and transgenic mice, Proc. Natl. Acad. Sci., (Apr. 1996), vol. 93, pp. 3346-3351.
Park, L., et al., Nox2-derived radicals contribute to neurovascular and behavioral dysfunction in mice overexpressing the amyloid precursor protein, Proc. Natl. Acad. Sci., (Jan. 29, 2008), vol. 105, No. 4, pp. 1347-1352.
Park, L., et al., Innate immunity receptor CD36 promotes cerebral amyloid angiopathy, PNAS, (Feb. 19, 2013), vol. 110, No. 8, pp. 3089-3094.
Pereira, D.J., et al., The Adeno-Associated Virus (AAV) Rep Protein Acts as both a Repressor and an Activator to Regulate AAV Transcription during a Productive Infection, Journal of Virology, (Feb. 1997), vol. 71, No. 2, pp. 1079-1088.
Qiu, C., et al., Epidemiology of Alzheimer's disease: occurrence, determinants, and strategies toward intervention, Dialogues in Clinical Neuroscience, (2009), vol. 11, No. 2, pp. 111-128.
Rhein, V., et al., Amyloid-β and tau synergistically impair the oxidative phosphorylation system in triple trangenic Alzheimer's disease mice, PNAS, (Nov. 24, 2009), vol. 106, No. 47, pp. 20057-20062.
Rutledge, E.A., et al., Infectious Clones and Vectors Derived from Adeno-Associated Virus (AAV) Serotypes Other Than AAV Type 2, Journal of Virology, (Jan. 1998), vol. 72, No. 1, pp. 309-319.
Selkoe, D.J., et al., Alzheimer's Disease, Cold Spring Har Perspect Biol, (2011), vol. 3, No. 7, pp. 1-17.
Sondhi, D., et al., Enhanced survival of the LINCL Mouse Following CLN2 Gene Transfer Using the rh. 10 Rhesus Macaque-derived Adeno-associated Virus Vector, Molecular Therapy, (Mar. 2007), vol. 15, No. 3, pp. 481-491.
Srivastava, A. Nucleotide Sequence and Organization of the Adeno-Associated Virus 2 Genome, Journal of Virology, (Feb. 1983), vol. 45, No. 2, pp. 555-564.
Wang, X., et al., Impaired Balance of Mitochondrial Fission and Fusion in Alzheimer's Disease, The Journal of Neuroscience, (Jul. 15, 2009), vol. 29, No. 28, pp. 9090-9103.
Watanabe, M., et al., AAVrh. 10-mediated genetic delivery of bevacizumab to the pleura to provide local anti-VEGF to suppress growth of metastatic lung tumors, Gene Therapy, (2010), vol. 17, pp. 1042-1051.
Worgall, S. et al., Treatment of Late Infantile Neuronal Ceroid Lipofuscinosis by CNS Administration of a Serotype 2 Adeno-Associated Virus Expressing CLN2 cDNA, Human Gene Therapy, (May 2008), vol. 19, pp. 463-474.
Wright, J.F., et al., Identification of Factors that Contribute to Recombinant AAV2 Particle Aggregation and Methods to Prevent Its Occurrence during Vector Purification and Formulation, Molecular Therapy, (Jul. 2005), vol. 12, No. 1, pp. 171-178.
Wu, P., et al., Mutational Analysis of the Adeno-Associated Virus Type 2 (AAV2) Capsid Gene and Construction of AAV2 Vectors with Altered Tropism, Journal of Virology, (Sep. 2000), vol. 74, No. 18, pp. 8635-8647.
Wu, Z., et al., Adeno-associated Virus Serotypes: Vector Toolkit for Human Gene Therapy, Molecular Therapy, (Sep. 2006), vol. 14, No. 3, pp. 316-327.
Zhou, P., et al., Prohibitin Reduces Mitochondrial Free Radical Production and Protects Brain Cells from Different Injury Modalities, The Journal of Neuroscience, (Jan. 11, 2012), vol. 32, No. 2, pp. 583-592.
Zhu, X., et al., Abnormal Mitochondrial Dynamics in the Pathogenesis of Alzheimer's Disease, Journal of Alzheimer's Disease, (2013), vol. 33, pp. S253-S262.
Ma, T., et al., Amyloid β: linking synaptic plasticity failure to memory disruption in Alzheimer's disease, Journal of Neurochemistry, (2012), vol. 120 (Suppl. 1), pp. 140-148.
Ausubel, F.M., et al., Current Protocols in Molecular Biology, John Wiley & Sons, Inc. NY, (Dec. 4, 2003), 336 pages.
Kramer, B.P., et al., Transgene Control Engineering in Mammalian Cells, Methods in Molecular Biology, (2005), vol. 308, pp. 123-143.
Wright, J. F., et al., Recombinant adeno-associated virus: Formulation challenges and strategies for a gene therapy vector, Current Opinion in Drug Discoery & Development, (2003), vol. 6, No. 2, pp. 174-178.
Howell, N., et al., mtDNA mutations and common neurodegenerative disorders, Trends in Genetics, (Nov. 2005), vol. 21, No. 11, pp. 583-586.
Reddy, P.H., et al., The role of mitochondria in neurodegenerative diseases: mitochondria as a therapeutic target in Alzheimer's disease, CNS Spectr., (Aug. 2009), vol. 14, 8 Suppl 7., pp. 8-18.
Onyango, I.G., et al., Endogenous oxidative stress in sporadic Alzheimer's disease neuronal cybrids reduces viability by increasing apoptosis through pro-death signaling pathways and is mimicked by oxidant exposure of control cybrids, Neurobiology of Disease, (2005), vol. 19, pp. 312-322.
Niwa, H., et al., Efficient selection for high-expression transfectants with a novel eukaryotic vector, Gene, (1991), vol. 108, pp. 193-200.
Im, D., et al., The AAV Origin Binding Protein Rep68 Is an ATP-Dependent Site-Specific Endonuclease with DNA Helicase Activity, Cell, (May 4, 1990), vol. 61, pp. 447-457.
Terry, R.D., et al., Senile Dementia of the Alzheimer Type, Ann Neurol, (1983), vol. 14, pp. 497-50.
Eckert, G.P., et al., Mitochondrial Dysfunction—A Pharmacological Target in Alzheimer's Disease, Mol Neurobiol, (2012), vol. 46, pp. 136-150.
Flotte, et al., New AAV Serotypes May Broaden the Therapeutic Pipeline to Human Gene Therapy, Molecular Therapy, (Jan. 2006), vol. 13, No. 1, 2 pages.
Glenner, G.G., et al., Alzheimer's Disease: Initial Report of the Purification and Characterization of a Novel Cerebrovascular Amyloid

(56) References Cited

OTHER PUBLICATIONS

Protein, Biochemical and Biophysical Research Communications, (May 16, 1984), vol. 120, No. 3, pp. 885-890.
Chapman P.F. et al., "Impaired Synaptic Plasticity and Learning in Aged Amyloid Precursor Protein Transgenic Mice", Nature Neuroscience 2(3):271-276 (Mar. 1999).
Hsiao K. et al., "Correlative Memory Deficits, Aβ Elevation, and Amyloid Plaques in Transgenic Mice", Science 274:99-102 (Oct. 4, 1996).
Pedersen W.A. et al., "Rosiglitazone Attenuates Learning and Memory Deficits in Tg2576 Alzheimer Mice", Experimental Neurology 199:265-273 (2006).
DiLorenzo F. et al., "Long-Term Potentiation-Like Cortical Plasticity is Disrupted in Alzheimer's Disease Patients Independently from Age of Onset", Annals of Neurology 80(2):202-210 (2016).
Iwata N. et al., "Global Brain Delivery of Neprilysin Gene by Intravascular Administration of AAV Vector in Mice", Scientific Reports 3:1472 (2013).

\* cited by examiner 5 days after BCCAO 5 days after BCCAO

SEQUENCE LISTING

```
<160> NUMBER OF SEQ ID NOS: 5

<210> SEQ ID NO 1
<211> LENGTH: 1039
<212> TYPE: DNA
<213> ORGANISM: Artificial Sequene
<220> FEATURE:
<223> OTHER INFORMATION: Prohibitin cDNA sequence (GenBank: BC095460.1)

<400> SEQUENCE: 1
ggaggtcaga gtggaagcag gtgtgagagg gtccagcaga aggaaacatg gctgccaaag      60
tgtttgagtc cattggcaag tttggcctgg ccttagctgt tgcaggaggc gtggtgaact     120
ctgccttata taatgtggat gctgggcaca gagctgtcat ctttgaccga ttccgtggag     180
```

```
tgcaggacat tgtggtaggg aagggactc attttctcat cccgtgggta cagaaaccaa    240
ttatctttga ctgccgttct cgaccacgta atgtgccagt catcactggt agcaaagatt    300
tacagaatgt caacatcaca ctgcgcatcc tcttccggcc tgtcgccagc cagcttcctc    360
gcatcttcac cagcatcgga gaggactatg atgagcgtgt gctgccgtcc atcacaactg    420
agatcctcaa gtcagtggtg gctcgctttg atgctggaga actaatcacc cagagagagc    480
tggtctccag gcaggtgagc gacgaccta cagagcgagc cgccaccttt gggctcatcc     540
tggatgacgt gtccttgaca catctgacct tcgggaagga gttcacagaa gcggtggaag    600
ccaaacaggt ggctcagcag gaagcagaga gggccagatt tgtggtggaa aaggctgagc    660
aacagaaaaa ggcggccatc atctctgctg agggcgactc caaggcagct gagctgattg    720
ccaactcact ggccactgca ggggatggcc tgatcgagct gcgcaagctg aagctgcag     780 aggacatcgc gtaccagctc tcacgctctc ggaacatcac ctacctgcca gcggggcagt    840
ccgtgctcct ccagctgccc cagtgagggc ccaccctgcc tgcacctccg cgggctgact    900
gggccacagc cccgatgatt cttaacacag ccttccttct gctcccaccc cagaaatcac    960
tgtgaaattt catgattggc ttaaagtgaa ggaaataaag gtaaaatcac ttcagatctc   1020
taaaaaaaaa aaaaaaaa                                                 1039
```

<210> SEQ ID NO 2
<211> LENGTH: 1342
<212> TYPE: DNA
<213> ORGANISM: Artificial Sequence
<220> FEATURE:
<223> OTHER INFORMATION: Prohibitin 2 cDNA sequence (GenBank: BC014766)

<400> SEQUENCE: 2

```
gcagtaccta agccggagcg gggtagaggc gggccggcac ccccttctga cctccagtgc     60
cgccggcctc aagatcagac atggcccaga acttgaagga cttggcggga cggctgcccg    120
ccgggccccg gggcatgggc acggccctga gctgttgct ggggggccggc gccgtggcct    180 acggtgtgcg cgaatctgtg ttcaccgtgg aaggcgggca cagagccatc ttcttcaatc    240
ggatcggtgg agtgcagcag gacactatcc tggccgaggg ccttcacttc aggatccctt    300
ggttccagta ccccattatc tatgacattc gggccagacc tcgaaaaatc tcctcccta    360 cagggctccaa agacctacag atggtgaata tctccctgcg agtgttgtct cgacccaatg    420
ctcaggagct tcctagcatg taccagcgcc tagggctgga ctacgaggaa cgagtgttgc    480
cgtccattgt caacgaggtg ctcaagagtg tggtggccaa gttcaatgcc tcacagctga    540
tcacccagcg ggcccaggta tccctgttga tccgccggga gctgacagag agggccaagg    600
acttcagcct catcctggat gatgtggcca tcacagagct gagctttagc cgagagtaca    660
cagctgctgt agaagccaaa caagtggccc agcaggaggc ccagcgggcc caattcttgg    720
tagaaaaagc aaagcaggaa cagcggcaga aaattgtgca ggccgagggt gaggccgagg    780
ctgccaagat gcttggagaa gcactgagca agaaccctgg ctacatcaaa cttcgcaaga    840
ttcgagcagc ccagaatatc tccaagacga tcgccacatc acagaatcgt atctatctca    900
cagctgacaa ccttgtgctg aacctacagg atgaaagttt caccagggga agtgacagcc    960
tcatcaaggg taagaaatga gcctagtcac caagaactcc accccagag gaagtggatc    1020 tgcttctcca gtttttgagg agccagccag gggtccagca cagccctacc ccgccccagt   1080
atcatgcgat ggtcccccac accggttccc tgaacccctc ttggattaag gaagactgaa   1140
```

```
gactagcccc ttttctgggg aattactttc ctcctccctg tgttaactgg ggctgtttggg    1200 gacagtgcgt gatttctcag tgatttccta cagtgttgtt ccctccctca aggctgggag    1260
gagataaaca ccaacccagg aattctcaat aaatttttat tacttaacct gaaaaaaaaa    1320
aaaaaaaaaa aaaaaaaaaa aa                                              1342
```

<210> SEQ ID NO 3
<211> LENGTH: 272
<212> TYPE: PRT
<213> ORGANISM: Artificial Sequence
<220> FEATURE:
<223> OTHER INFORMATION: Prohibitin amino acid sequence

<400> SEQUENCE: 3

```
Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Gln Arg Glu
    130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205

Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
            260                 265                 270
```

<210> SEQ ID NO 4
<211> LENGTH: 299
<212> TYPE: PRT
<213> ORGANISM: Artificial Sequence
<220> FEATURE:
<223> OTHER INFORMATION: Prohibitin 2 amino acid sequence (UniProtKB/
      Swiss-Prot: PHB2_HUMAN, Q99623)

<400> SEQUENCE: 4

```
Met Ala Gln Asn Leu Lys Asp Leu Ala Gly Arg Leu Pro Ala Gly Pro
1               5                  10                  15

Arg Gly Met Gly Thr Ala Leu Lys Leu Leu Gly Ala Gly Ala Val
            20                  25                  30

Ala Tyr Gly Val Arg Glu Ser Val Phe Thr Val Glu Gly Gly His Arg
                35                  40                  45

Ala Ile Phe Phe Asn Arg Ile Gly Gly Val Gln Gln Asp Thr Ile Leu
    50                  55                  60

Ala Glu Gly Leu His Phe Arg Ile Pro Trp Phe Gln Tyr Pro Ile Ile
65                  70                  75                  80

Tyr Asp Ile Arg Ala Arg Pro Arg Lys Ile Ser Ser Pro Thr Gly Ser
                85                  90                  95

Lys Asp Leu Gln Met Val Asn Ile Ser Leu Arg Val Leu Ser Arg Pro
                100                 105                 110

Asn Ala Gln Glu Leu Pro Ser Met Tyr Gln Arg Leu Gly Leu Asp Tyr
            115                 120                 125

Glu Glu Arg Val Leu Pro Ser Ile Val Asn Glu Val Leu Lys Ser Val
130                 135                 140

Val Ala Lys Phe Asn Ala Ser Gln Leu Ile Thr Gln Arg Ala Gln Val
145                 150                 155                 160

Ser Leu Leu Ile Arg Arg Glu Leu Thr Glu Arg Ala Lys Asp Phe Ser
                165                 170                 175

Leu Ile Leu Asp Asp Val Ala Ile Thr Glu Leu Ser Phe Ser Arg Glu
                180                 185                 190

Tyr Thr Ala Ala Val Glu Ala Lys Gln Val Ala Gln Gln Glu Ala Gln
            195                 200                 205

Arg Ala Gln Phe Leu Val Glu Lys Ala Lys Gln Glu Gln Arg Gln Lys
210                 215                 220

Ile Val Gln Ala Glu Gly Glu Ala Glu Ala Lys Met Leu Gly Glu
225                 230                 235                 240

Ala Leu Ser Lys Asn Pro Gly Tyr Ile Lys Leu Arg Lys Ile Arg Ala
                245                 250                 255

Ala Gln Asn Ile Ser Lys Thr Ile Ala Thr Ser Gln Asn Arg Ile Tyr
            260                 265                 270

Leu Thr Ala Asp Asn Leu Val Leu Asn Leu Gln Asp Glu Ser Phe Thr
            275                 280                 285

Arg Gly Ser Asp Ser Leu Ile Lys Gly Lys Lys
290                 295

<210> SEQ ID NO 5
<211> LENGTH: 653
<212> TYPE: DNA
<213> ORGANISM: Artificial Sequence
<220> FEATURE:
<223> OTHER INFORMATION: CMV promoter sequence

<400> SEQUENCE: 5
ctagttatta atagtaatca attacggggt cattagttca tagcccatat atggagttcc      60
gcgttacata acttacggta atggcccgc ctggctgacc gcccaacgac ccccgcccat     120
tgacgtcaat aatgacgtat gttcccatag taacgtcaat agggactttc cattgacgtc     180
aatgggtgga gtatttacgg taaactgccc acttggcagt acatcaagtg tatcatatgc     240
caagtacgcc ccctattgac gtcaatgacg gtaaatggcc cgcctggcat tatgcccagt     300
acatgacctt atgggacttt cctacttggc agtacatcta cgtattagtc atcgctatta     360
```

```
ccatggtgat gcggttttgg cagtacatca atgggcgtgg atagcggttt gactcacggg      420
gatttccaag tctccacccc attgacgtca atgggagttt gttttgcacc aaaatcaacg      480
ggactttcca aaatgtcgta acaactccgc cccattgacg caaatgggcg gtaggcgtgt      540
acggtgggag gtctatataa gcagagctcg tttagtgaac cgtcagatcg cctggagacg      600
ccatccacgc tgttttgacc tccatagaag acaccgggac cgatccagcc tcc            653
```

GENE THERAPY FOR ALZHEIMER'S AND OTHER NEURODEGENERATIVE DISEASES AND CONDITIONS

This application claims the benefit of priority to U.S. Provisional Application Ser. No. 61/898,776, filed on Nov. 1, 2013, which is incorporated by reference into the present application.

GOVERNMENT FUNDING

This invention was made with government support under NS037853 and NS067078 awarded by the National Institutes of Health (NIH). The government has certain rights in the invention.

INCORPORATION BY REFERENCE OF SEQUENCE LISTING

The Sequence Listing in the ASCII text file, named as 30592_SEQ.txt of 10 kilobytes, created on Oct. 27, 2014, and submitted to the United States Patent and Trademark Office via EFS-Web, is incorporated herein by reference.

BACKGROUND OF THE INVENTION

Alzheimer's disease (AD) is the most common form of age-dependent cognitive impairment (BROOKMEYER, et al., Alzheimers Dement, 3(3):186-191 (2007); QIU, et al., Dialogues Clin Neurosci, 11(2):111-128 (2009)). The key neuropathological features of AD include two extracellular protein aggregates: neurofibrillary tangles and amyloid beta (Aβ) plaques (GLENNER, et al., Biochem Biophys Res Commun, 120(3):885-890 (1984); SELKOE, Cold Spring Harb Perspect Biol, 3(7) (2011); TERRY, et al., Ann Neurol, 14(5):497-506 (1983)). AD is characterized by loss of neurons and synapses in the cerebral cortex and certain subcortical regions. This loss results in gross atrophy of the affected regions, including degeneration in the temporal lobe and parietal lobe, and parts of the frontal cortex and cingulate gyrus. Both amyloid plaques and neurofibrillary tangles found in brains of subjects afflicted with AD.

Although it remains largely unknown how the disease is initiated, the aberrant accumulation of Aβ in brain regions involved in cognitive function is believed to play a causative role in AD development.

Aβ causes significant pathological changes including dysfunction in energy metabolism, oxidative stress and inflammation (DURAN-GONZALEZ, et al., Neurobiol Aging, 34(8):2071-2076 (2013); ONYANGO, et al., Neurobiol Dis, 19(1-2):312-322 (2005)), ultimately resulting in the synaptic dysfunction underlying cognitive impairment (CLEARY, et al., Nat Neurosci, 8(1):79-84 (2005)). Mitochondria have emerged as a central organelle in the pathobiology of AD (ECKERT, et al., Mol Neurobiol, 4(1):136-150 (2012); REDDY, et al., CNS Spectr, 14(8 Suppl 7):8-13, discussion 16-18 (2009)). Mitochondrial defects in AD include increased reactive oxygen species (ROS) production (MANCZAK, et al., Hum Mol Genet, 15(9):1437-1449 (2006)), accumulation of mitochondrial DNA mutations (HOWELL et al. 2005), impairment in energy metabolism (ANANDATHEERTHAVARADA, et al., J Cell Biol, 161 (1):41-54 (2003)), reduced mitochondrial respiratory chain complex activity (RHEIN, et al., Proc Natl Acad Sci USA, 106(47):20057-20062 (2009)), deregulation of calcium homeostasis, decreased mitochondrial transport, and imbalanced mitochondrial fission and fusion (WANG, et al., J Neurosci, 29(28):9090-9103 (2009); ZHU, et al., J. Alzheimers Dis, 33(Suppl 1):S253-262 (2013)). Despite the extensive evidence pointing to the role of mitochondria in AD, it has been difficult to prove that mitochondrial therapies are effective in reversing or slowing down AD progression. Mitochondrially-targeted anti-oxidants have been used successfully in AD animal models, but their clinical efficacy remains to be determined. Small molecules, such as MitoQ, could act as ROS scavengers, but do not appear to fundamentally prevent mitochondrial dysfunction or restore damaged mitochondria in AD.

Modulation of mitochondrial proteins involved in mitochondrial structure and function is a novel approach to achieve neuroprotection by counteracting the effects of noxious factors that target the organelles, such as Aβ. Genetic deletion of cyclophilin D (CypD), a regulator of the $Ca^{2+}$-dependent permeability transition pore (MPTP), in APP mice resulted in improved mitochondrial function, morphology and transport in vitro, reduced Aβ and oxidative stress-induced neuronal cell death, and substantially improved learning and memory and synaptic function in vivo, in an AD mouse model (DU, et al., Nat Med, 14(10): 1097-105 (2008)). Unfortunately, CypD is a highly conserved protein that plays an important role in $Ca^{2+}$ regulation, and its complete deletion may lead to unforeseen consequences on cell function and survival. On the other hand, CypD function cannot be only partially reduced to achieve an effect on MPTP, since even half the amount of the protein is sufficient to produce normal MPTP responses. Therefore, an alternative protein approach is needed to modulate mitochondrial stability in AD.

Prohibitin is an essential mitochondrial protein that has been implicated in a wide variety of functions in many cell types (ZHOU, et al., J Neurosci, 32(2):583-592 (2012)). Prohibitins are assembled into a ring-like structure with 16-20 alternating Phb1 and Phb2 subunits in the inner mitochondrial membrane (MERKWIRTH, et al., PLOS Genetics, 8(11):1-13 (2012)). Prohibitin gene silencing increases the vulnerability of neurons to injury, associated with a loss of mitochondrial membrane potential and an increase mitochondrial production of ROS (ZHOU, et al., J Neurosci, 32(2):583-592 (2012)). Similarly, loss of prohibitin has been shown to lead to tau hyperphosphorylation and neurodegeneration (MERKWIRTH, et al., PLOS Genetics, 8(11):1-13 (2012)). However, the art has not demonstrated the ability of prohibitin to restore cognitive function in subjects showing cognitive dysfunction resulting from a neurological disease.

Disclosed herein are new compositions and gene therapy methods to restore cognitive function in subjects suffering from AD and other neurodegenerative diseases and conditions by increasing the expression of exogenous prohibitin in neurons of the brains of the subjects.

SUMMARY OF THE INVENTION

The present invention provides a method for treating a subject having a neurological disorder, by expressing exogenous prohibitin in the brain of the subject. The neurological disorder can be, for example, Alzheimer's disease.

In some embodiments, the subject suitable for treatment in accordance with the present method has been clinically diagnosed with a neurological disorder. In some embodiments, the subject suitable for treatment in accordance with the present method shows one or more of cognitive, functional, biochemical or structural defects. A cognitive defect includes impairment in one or more of conditioned memory, spatial memory, contextual memory, memory retention, contextual learning, and conditioned learning. Biochemical defects include, for example, tau hyperphosphorylation and accumulation of Aβ. Structural defects include amyloid plaques, diffuse amyloid plaques, neurofibrillary tangles, neuronal loss, and synaptic loss. Functional defects include impairment in long-term potentiation of neurons.

The exogenous prohibitin can be expressed in the brain of the subject having a neurological disorder by using an adeno-associated virus (AAV) nucleic acid vector ("AAV vector" or "recombinant AAV vector"), which encodes, in a 5' to 3' direction:
   a. a first adeno-associated viral inverted terminal repeat (ITR),
   b. a promoter controlling the expression of a nucleic acid sequence encoding an exogenous prohibitin,
   c. a nucleic acid encoding an exogenous prohibitin, and
   d. a second adeno-associated viral ITR.

The present invention provides exogenous prohibitin molecules suitable for treating a subject having a neurological disorder. For example, the exogenous prohibitin may be encoded by the nucleic acid sequence set forth in SEQ ID NO: 1. Alternatively, the exogenous prohibitin may be encoded by the nucleic acid sequence set forth in SEQ ID NO: 2.

The present invention provides AAV vectors suitable for use in treating a subject having a neurological disorder. For example, the AAV vector can be the AAV2 serotype. Alternatively, the AAV vector can be the AAVrh.10 serotype. Alternatively, the AAV vector can be the AAV8 serotype. Alternatively, the AAV vector can be the AAV9 serotype.

Delivery of a recombinant AAV vector is in most embodiments achieved via AAV virions containing the recombinant AAV vector. In some embodiments, an AAV vector which comprises a prohibitin coding sequenceis delivered by administering virions containing the AAV vector into the brain of a subject, and the prohibitin is expressed in the brain of the subject. The AAV vectors may be delivered via AAV virions to specific regions of the subject's brain. For example, the AAV vectors may be delivered (for example, injected) via AAV virions intracerebrally or intrathecally. Alternatively, the AAV vectors may be delivered via AAV virions systemically. The expression of the exogenous prohibitin may be targeted to a specific region within the subject's brain. Alternatively, the expression of the exogenous prohibitin may be targeted to a specific cell type within the subject's brain.

BRIEF DESCRIPTION OF THE DRAWINGS

FIG. 1 (B) shows an alternate representation of a nucleic acid vector, lacking the eGFP sequence.

FIG. 2, (B) and (C) shows the quantitative analysis of DHE fluorescence in the two peaks.

FIG. 3 (B) shows cell morphology in hippocampus 5 days after BCCAO. FIG. 3 (C) depicts a diagram illustrating the location of cell injury after BCCAO in a 3D reconstruction of the hippocampus, and the locations of 5 hippocampal sections. FIG. 3 (D) shows the percentage of dead CA1 neurons in hippocampal slices obtained from animals treated with a prohibitin expressing vector (right columns) and animals treated with a control vector (left columns).

FIG. 4 (A) shows brain sections prepared 3 weeks post procedure to assess the level and location of GFP expression. FIG. 4 (B) shows Western blots, showing PHB protein levels in hippocampal tissue injected with AAV-GFP (vector) and AAV-PHB (PHB). FIG. 4 (C) is a quantitation of the protein band in FIG. 4 (B).

FIG. 5 (C) shows cumulative data showing mean fEPSP slopes 80 minutes post-HFS based on the LTP experiments in panel A and B. The white column shows cumulative data from AAV-vector-treated animals. The black column shows data from AAV-PHB-treated animals.

DETAILED DESCRIPTION

Figure 1:
FIG. 1 (A) shows a representation of a nucleic acid vector used in one embodiment of the present invention.
Figure 1:
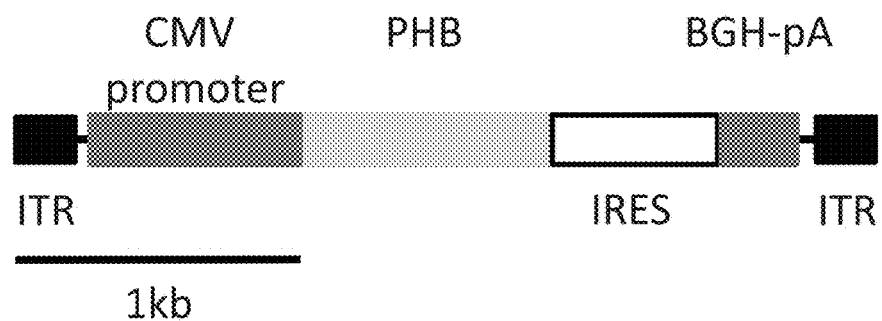

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

In one embodiment, the present invention provides a method for treating a subject having a neurological disorder, comprising delivering a gene transfer vector that contains a nucleic acid encoding an exogenous prohibitin to the brain of the subject. The exogenous prohibitin is expressed in the brain of the subject in an amount effective to treat the neurological disorder.

Exogenous Prohibitin.

The term "prohibitin" or "PHB" as used herein, refers to a member of the prohibitin family. Members of the prohibitin family include, for example, human prohibitin, having the amino acid sequence set forth in SEQ ID NO: 3 (UniProtKB/Swiss-Prot: PHB_HUMAN, P35232), human prohibitin 2, having the amino acid sequence set forth in SEQ ID NO: 4 (UniProtKB/Swiss-Prot: PHB2_HUMAN, Q99623). "Prohibitin" also includes alternatively spliced isoforms (including but not limited to UniProtKB/Swiss-Prot reference proteins P35232-88, P35232-105,), homologs in non-human species, peptide fragments of any of the foregoing. "Prohibitin" also includes alternate conformations, and/or post-translationally modified proteins or peptides of any of the foregoing, including but not limited to phosphorylations at serine and threonine residues, ubiquitinations, glycations, sialylations, and the like.

The term "nucleic acid sequence" as used herein, refers to a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides.

The term "sequence homology" as used herein refers to the proportion of base matches between two nucleotide sequences or the proportion of amino acid matches between two amino acid sequences. When sequence homology is expressed as a percentage, e.g., 50%, the percentage denotes the proportion of matches in a portion of one sequence in comparison to a portion of another sequence. Gaps (in either of the two sequences) are permitted to maximize matching; gap lengths of 15 bases or less are usually used, 6 bases or less are used more frequently, with 2 bases or less used even more frequently. The term "sequence identity" means that sequences are identical (i.e., on a nucleotide-by-nucleotide basis for nucleic acids or amino-acid-by-amino-acid basis for polypeptides) over a window of comparison. The term "percentage of sequence identity" is calculated by comparing two optimally aligned sequences over the comparison window, determining the number of positions at which the identical amino acids occurs in both sequences to yield the number of matched positions, dividing the number of matched positions by the total number of positions in the comparison window, and multiplying the result by 100 to yield the percentage of sequence identity. Methods to calculate sequence identity are known to those of skill in the art and described in further detail below.

The present invention provides a method for treating a subject having a neurological disorder, such as, for example, Alzheimer's disease, by expressing exogenous prohibitin in the brain of the subject. The exogenous prohibitin may be encoded by the nucleic acid sequence set forth in SEQ ID NO: 1. Alternatively, the exogenous prohibitin may be encoded by the nucleic acid sequence set forth in SEQ ID NO: 2.

In another embodiment, the nucleic acid sequence which encodes an exogenous prohibitin has at least about 95% sequence homology to the nucleotide sequence set forth in SEQ ID NO: 1 or the nucleotide sequence set forth in SEQ ID NO: 2.

In another embodiment, the nucleic acid sequence which encodes an exogenous prohibitin has at least about 90% sequence homology to the nucleotide sequence set forth in SEQ ID NO: 1 or the nucleotide sequence set forth in SEQ ID NO: 2.

In another embodiment, the nucleic acid sequence which encodes an exogenous prohibitin has at least about 85% sequence homology to the nucleotide sequence set forth in SEQ ID NO: 1 or the nucleotide sequence set forth in SEQ ID NO: 2.

In another embodiment, the nucleic acid sequence which encodes an exogenous prohibitin has at least about 80% sequence homology to the nucleotide sequence set forth in SEQ ID NO: 1 or the nucleotide sequence set forth in SEQ ID NO: 2.

The nucleic acid sequence that encodes an exogenous prohibitin can be generated using methods known in the art. For example, nucleic acid sequences, polypeptides, and proteins may be recombinantly produced using standard recombinant DNA methodology (see, e.g., Sambrook et al., Molecular Cloning: A Laboratory Manual, 3rd ed., Cold Spring Harbor Press, Cold Spring Harbor, N.Y., 2001; and Ausubel et al., Current Protocols in Molecular Biology, Greene Publishing Associates and John Wiley & Sons, NY, 1994). Further, a synthetically produced nucleic acid sequence which encodes an PHB, may be isolated and/or purified from a source, such as a bacterium, an insect, or a mammal, e.g., a rat, a human, etc. Methods of isolation and purification are well-known in the art. Alternatively, the nucleic acid sequences described herein can be commercially synthesized. In this respect, the nucleic acid sequence can be synthetic, recombinant, isolated, and/or purified.

The nucleic acid sequence that encodes an exogenous prohibitin may be identified by extracting RNA from cells. In cases where an exogenous prohibitin is identified from RNA extracted from cells, cDNA can be produced by reverse transcription and PCR amplification of the light and heavy chains and is carried out using a rapid amplification of cDNA ends (RACE) strategy in combination with specific primers for conserved regions in the constant domains.

The nucleic acid sequence that encodes an exogenous prohibitin may also be fully or partly humanized by means known in the art.

Resulting nucleic acid sequences encoding an exogenous prohibitin may be optimized for high expression levels in mammalian cells, by any suitable method in the art, such as, for example through removal of RNA instability elements.

```
SEQ ID NO: 1: Prohibitin cDNA sequence (GenBank: BC095460.1)
      1    ggaggtcaga gtggaagcag gtgtgagagg gtccagcaga aggaaacatg gctgccaaag 61    tgtttgagtc cattggcaag tttggcctgg ccttagctgt tgcaggaggc gtggtgaact 121    ctgccttata taatgtggat gctgggcaca gagctgtcat ctttgaccga ttccgtggag 181    tgcaggacat tgtggtaggg gaagggactc attttctcat cccgtgggta cagaaaccaa 241    ttatctttga ctgccgttct cgaccacgta atgtgccagt catcactggt agcaaagatt 301    tacagaatgt caacatcaca ctgcgcatcc tcttccggcc tgtcgccagc cagcttcctc 361    gcatcttcac cagcatcgga gaggactatg atgagcgtgt gctgccgtcc atcacaactg 421    agatcctcaa gtcagtggtg gctcgctttg atgctggaga actaatcacc cagagagagc 481    tggtctccag gcaggtgagc gacgacctta cagagcgagc cgccacccttt gggctcatcc
```

```
541  tggatgacgt gtccttgaca catctgacct tcgggaagga gttcacagaa gcggtggaag 601  ccaaacaggt ggctcagcag gaagcagaga gggccagatt tgtggtggaa aaggctgagc 661  aacagaaaaa ggcggccatc atctctgctg agggcgactc caaggcagct gagctgattg 721  ccaactcact ggccactgca ggggatggcc tgatcgagct cgcaagctg aagctgcag 781  aggacatcgc gtaccagctc tcacgctctc ggaacatcac ctacctgcca gcggggcagt 841  ccgtgctcct ccagctgccc cagtgagggc ccaccctgcc tgcacctccg cgggctgact 901  gggccacagc ccgatgatt cttaacacag ccttccttct gctcccaccc agaaatcac 961  tgtgaaattt catgattggc ttaaagtgaa ggaaataaag gtaaaatcac ttcagatctc 1021 taaaaaaaaa aaaaaaaaa
```

SEQ ID NO: 2: Prohibitin 2 cDNA sequence (GenBank: BC014766)
```
   1 gcagtaccta agccggagcg gggtagaggc gggccggcac cccttctga cctccagtgc 61 cgccggcctc aagatcagac atgggccaga acttgaagga cttggcggga cggctgcccg 121 ccgggccccg gggcatgggc acggccctga gctgttgct ggggccggc gccgtggcct 181 acggtgtgcg cgaatctgtg ttcaccgtgg aaggcgggca cagagccatc ttcttcaatc 241 ggatcggtgg agtgcagcag gacactatcc tggccgaggg ccttcacttc aggatcccctt 301 ggttccagta ccccattatc tatgacattc gggccagacc tcgaaaaatc cctcccccta 361 caggctccaa agacctcag atggtgaata tctccctgcg agtgttgtct cgacccaatg 421 ctcaggagct tcctagcatg taccagcgcc tagggctgga ctacgaggaa cgagtgttgc 481 cgtccattgt caacgaggtg ctcaagagtg tggtggccaa gttcaatgcc tcacagctga 541 tcacccagcg ggcccaggta tccctgttga tccgccggga gctgacagag agggccaagg 601 acttcagcct catcctggat gatgtggcca tcacagagct gagctttagc cgagagtaca 661 cagctgctgt agaagccaaa caagtggccc agcaggaggc ccagcgggcc caattcttgg 721 tagaaaaagc aaagcaggaa cagcggcaga aaattgtgca ggccgagggt gaggccgagg 781 ctgccaagat gcttggagaa gcactgagca agaaccctgg ctacatcaaa cttcgcaaga 841 ttcgagcagc ccagaatatc tccaagacga tcgccacatc acagaatcgt atctatctca 901 cagctgacaa ccttgtgctg aacctacagg atgaaagttt caccagggga agtgacagcc 961 tcatcaaggg taagaaatga gcctagtcac caagaactcc accccccagag gaagtggatc 1021 tgcttctcca gtttttgagg agccagccag gggtccagca cagccctacc ccgcccagt 1081 atcatgcgat ggtccccac accggttccc tgaaccccctc ttggattaag gaagactgaa 1141 gactagcccc ttttctgggg aattactttc ctcctccctg tgttaactgg ggctgttggg 1201 gacagtgcgt gatttctcag tgatttccta cagtgttgtt ccctccctca aggctgggag 1261 gagataaaca ccaacccagg aattctcaat aaattttat tacttaaacct gaaaaaaaa 1321 aaaaaaaaaa aaaaaaaaa aa
```

SEQ ID NO: 3: Prohibitin amino acid sequence
MAAKVFESIG KFGLALAVAG GVVNSALYNV DAGHRAVIFD RFRGVQDIVV GEGTHFLIPW

VQKPIIFDCR SRPRNVPVIT GSKDLQNVNI TLRILFRPVA SQLPRIFTSI GEDYDERVLP

SITTEILKSV VARFDAGELI TQRELVSRQV SDDLTERAAT FGLILDDVSL THLTFGKEFT

EAVEAKQVAQ QEAERARFVV EKAEQQKKAA IISAEGDSKA AELIANSLAT AGDGLIELRK

LEAAEDIAYQ LSRSRNITYL PAGQSVLLQL PQ

SEQ ID NO: 4: Prohibitin 2 amino acid sequence
(UniProtKB/Swiss-Prot: PHB2_HUMAN, Q99623)
MAQNLKDLAG RLPAGPRGMG TALKLLLGAG AVAYGVRESV FTVEGGHRAI FFNRIGGVQQ -continued

```
DTILAEGLHF RIPWFQYPII YDIRARPRKI SSPTGSKDLQ MVNISLRVLS RPNAQELPSM

YQRLGLDYEE RVLPSIVNEV LKSVVAKFNA SQLITQRAQV SLLIRRELTE RAKDFSLILD

DVAITELSFS REYTAAVEAK QVAQQEAQRA QFLVEKAKQE QRQKIVQAEG EAEAAKMLGE

ALSKNPGYIK LRKIRAAQNI SKTIATSQNR IYLTADNLVL NLQDESFTRG SDSLIKGKK
```

Gene Transfer Vectors Suitable for Use According to the Methods of the Present Invention.

In one embodiment, the exogenous prohibitin is expressed in the brain of a subject having a neurological disorder by using a gene transfer vector, which contains a nucleic acid sequence encoding a prohibitin.

Various aspects of the inventive gene transfer vector and method are discussed below. Although each parameter is discussed separately, the gene transfer vector and method comprise combinations of the parameters set forth below to overexpress exogenous prohibitin in a subject having a neurological disorder. Accordingly, any combination of parameters can be used according to the inventive gene transfer vector and the method of the present invention.

The term "gene transfer vector", as used herein refers to any molecule or composition that has the ability to carry an exogenous nucleic acid sequence into a suitable host cell where synthesis of the encoded protein takes place. Typically and preferably, a gene transfer vector is a nucleic acid molecule that has been engineered, using recombinant DNA techniques that are known in the art, to incorporate the heterologous nucleic acid sequence. Desirably, the gene transfer vector is comprised of DNA. Examples of suitable DNA-based gene transfer vectors include plasmids and viral vectors. However, gene transfer vectors that are not based on nucleic acids, such as liposomes, are also known and used in the art. The gene transfer vector suitable for use herein can be based on a single type of nucleic acid (e.g., a plasmid) or non-nucleic acid molecule (e.g., a lipid or a polymer). The inventive gene transfer vector can be integrated into the host cell genome, or can be present in the host cell in the form of an episome.

Preferably, the gene transfer vector is a viral vector. Suitable viral vectors include, for example, retroviral vectors, herpes simplex virus (HSV)-based vectors, parvovirus-based vectors, e.g., adeno-associated virus (AAV)-based vectors, AAV-adenoviral chimeric vectors, and adenovirus-based vectors. These viral vectors can be prepared using standard recombinant DNA techniques described in, for example, Sambrook et al., Molecular Cloning, a Laboratory Manual, 3rd edition, Cold Spring Harbor Press, Cold Spring Harbor, N.Y. (2001), and Ausubel et al., Current Protocols in Molecular Biology, Greene Publishing Associates and John Wiley & Sons, New York, N.Y. (1994).

In one embodiment, the exogenous prohibitin is expressed in the brain of a subject having a neurological disorder by using an adeno-associated virus (AAV) nucleic acid vector (or "AAV vector" as used herein), which encodes, in a 5' to 3' direction:
  a. a first adeno-associated viral inverted terminal repeat (ITR),
  b. a promoter controlling the expression of a nucleic acid sequence encoding an exogenous prohibitin,
  c. a nucleic acid encoding an exogenous prohibitin, and
  d. a second adeno-associated viral ITR.

In one embodiment, the gene transfer vector is the vector depicted in FIG. 1 (A). In an alternate embodiment, the gene transfer vector is the vector depicted in FIG. 1 (B).

Adeno-associated virus is a member of the Parvoviridae family and comprises a linear, single-stranded DNA genome of less than about 5,000 nucleotides. AAV requires co-infection with a helper virus (i.e., an adenovirus or a herpes virus), or expression of helper genes, for efficient replication. AAV vectors used for administration of therapeutic nucleic acids typically have approximately 96% of the parental genome deleted, such that only the terminal repeats (ITRs), which contain recognition signals for DNA replication and packaging, remain. This eliminates immunologic or toxic side effects due to expression of viral genes. In addition, delivering specific AAV proteins to producing cells enables integration of the AAV vector comprising AAV ITRs into a specific region of the cellular genome, if desired (see, e.g., U.S. Pat. Nos. 6,342,390 and 6,821,511). Host cells comprising an integrated AAV genome show no change in cell growth or morphology (see, for example, U.S. Pat. No. 4,797,368).

The AAV ITRs flank the unique coding nucleotide sequences for the non-structural replication (Rep) proteins and the structural capsid (Cap) proteins (also known as virion proteins (VPs)). The terminal 145 nucleotides are self-complementary and are organized so that an energetically stable intramolecular duplex forming a T-shaped hairpin may be formed. These hairpin structures function as an origin for viral DNA replication by serving as primers for the cellular DNA polymerase complex. The Rep genes encode the Rep proteins Rep78, Rep68, Rep52, and Rep40. Rep78 and Rep68 are transcribed from the p5 promoter, and Rep 52 and Rep40 are transcribed from the p19 promoter. The Rep78 and Rep68 proteins are multifunctional DNA binding proteins that perform helicase and nickase functions during productive replication to allow for the resolution of AAV termini (see, e.g., IM, et al., Cell, 61(3):447-457 (1990)). These proteins also regulate transcription from endogenous AAV promoters and promoters within helper viruses (see, e.g., PEREIRA, et al., J Virol., 71:1079-1088 (1997)). The other Rep proteins modify the function of Rep78 and Rep68. The cap genes encode the capsid proteins VP1, VP2, and VP3. The cap genes are transcribed from the p40 promoter.

The AAV vector can be generated using any AAV serotype known in the art. Several AAV serotypes and over 100 AAV variants have been isolated from adenovirus stocks or from human or nonhuman primate tissues (reviewed in, e.g., WU, et al., Molecular Therapy, 14(3):316-327 (2006)). Generally, the AAV serotypes have genomic sequences of significant homology at the nucleic acid sequence and amino acid sequence levels, such that different serotypes have an identical set of genetic functions, produce virions which are essentially physically and functionally equivalent, and replicate and assemble by practically identical mechanisms. AAV serotypes 1-6 and 7-9 are defined as "true" serotypes, in that they do not efficiently cross-react with neutralizing sera specific for all other existing and characterized serotypes. In contrast, AAV serotypes 6, 10 (also referred to as Rh10), and 11 are considered "variant" serotypes as they do not adhere to the definition of a "true" serotype. AAV serotype 2 (AAV2) has been used extensively for gene therapy applications due to its lack of pathogenicity, wide range of infectivity, and ability to establish long-term transgene expression (see, e.g., CARTER, Hum. Gene Ther., 16:541-550 (2005); WU, et al., Molecular Therapy, 14(3): 316-327 (2006)). Genome sequences of various AAV serotypes and comparisons thereof are disclosed in, for example, GenBank Accession numbers U89790, J01901, AF043303, and AF085716; Chiorini et al., J. Virol., 71: 6823-33 (1997); Srivastava et al., J. Virol., 45: 555-64 (1983); Chiorini et al., J. Virol., 73: 1309-1319 (1999); Rutledge et al., J. Virol., 72: 309-319 (1998); and Wu et al., J. Virol., 74: 8635-47 (2000)).

AAV rep and ITR sequences are particularly conserved across most AAV serotypes. For example, the Rep78 proteins of AAV2, AAV3A, AAV3B, AAV4, and AAV6 are reportedly about 89-93% identical (see BANTEL-SCHAAL et al., J. Virol. 73(2): 939-947 (1999)). It has been reported that AAV serotypes 2, 3A, 3B, and 6 share about 82% total nucleotide sequence identity at the genome level (BANTEL-SCHAAL et al., J. Virol. 73(2): 939-947 (1999)). Moreover, the rep sequences and ITRs of many AAV serotypes are known to efficiently cross-complement (i.e., functionally substitute) corresponding sequences from other serotypes during production of AAV particles in mammalian cells.

Generally, the cap proteins, which determine the cellular tropicity of the AAV particle, and related cap protein-encoding sequences, are significantly less conserved than Rep genes across different AAV serotypes. In view of the ability Rep and ITR sequences to cross-complement corresponding sequences of other serotypes, the AAV vector can comprise a mixture of serotypes and thereby be a "chimeric" or "pseudotyped" AAV vector. A chimeric AAV vector typically comprises AAV capsid proteins derived from two or more (e.g., 2, 3, 4, etc.) different AAV serotypes. In contrast, a pseudotyped AAV vector comprises one or more ITRs of one AAV serotype packaged into a capsid of another AAV serotype. Chimeric and pseudotyped AAV vectors are further described in, for example, U.S. Pat. No. 6,723,551; FLOTTE, Mol. Ther, 13(1):1-2 (2006); GAO, et al., J. Virol., 78:6381-6388 (2004); GAO et al., Proc. Natl. Acad. Sci. USA, 99:11854-11859 (2002); DE et al., Mol. Ther., 13:67-76 (2006); and GAO et al., Mol. Ther., 13:77-87 (2006).

In one embodiment, the AAV vector is generated using an AAV that infects humans (e.g., AAV2). Alternatively, the AAV vector is generated using an AAV that infects non-human primates, such as, for example, the great apes (e.g., chimpanzees), Old World monkeys (e.g., macaques), and New World monkeys (e.g., marmosets). Preferably, the AAV vector is generated using an AAV that infects a non-human primate pseudotyped with an AAV that infects humans. Examples of such pseudotyped AAV vectors are disclosed in, e.g., CEARLEY, et al., Molecular Therapy, 13:528-537 (2006). In one embodiment, an AAV vector can be generated which comprises a capsid protein from an AAV that infects rhesus macaques pseudotyped with AAV2 inverted terminal repeats (ITRs). In a particularly preferred embodiment, the inventive AAV vector comprises a capsid protein from AAV10 (also referred to as "AAVrh.10"), which infects rhesus macaques pseudotyped with AAV2 ITRs (see, e.g., WATANABE et al., Gene Ther., 17(8):1042-1051 (2010); MAO, et al., Hum. Gene Therapy, 22:1525-1535 (2011)).

Additional components can be included that do not materially affect the AAV vector. Examples include genetic elements such as epitope tags, poly(A) sequences or restriction enzyme sites that facilitate manipulation of the vector in vitro.

In addition to the nucleic acid sequence encoding the exogenous prohibitin, gene transfer vectors suitable for use in the present invention may also contain expression control sequences, such as promoters, enhancers, polyadenylation signals, transcription terminators, internal ribosome entry sites (IRES), and the like, that provide for the expression of the prohibitin in the subject's cells. Exemplary expression control sequences are known in the art and described in, for example, Goeddel, Gene Expression Technology: Methods in Enzymology, Vol. 185, Academic Press, San Diego, Calif. (1990).

A large number of promoters, including constitutive, inducible, tissue specific, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, and the RSV promoter. Inducible promoters include, for example, the Tet system (U.S. Pat. Nos. 5,464,758 and 5,814,618), the Ecdysone inducible system (NO, et al., Proc. Natl. Acad. Sci USA, 93:3346-3351 (1996)), the T-REX™ system (Invitrogen, Carlsbad, Calif.), LACSWITCH™ System (Stratagene, San Diego, Calif.), and the Cre-ERT tamoxifen inducible recombinase system (INDRA, et al., Nuc. Acid. Res., 27:4324-4327 (1999); INDRA, et al., Nuc. Acid. Res., 28:e99 (2000); U.S. Pat. No. 7,112,715; and KRAMER, et al., Methods Mol. Biol., 308: 23-144 (2005)).

In one embodiment, the promoter is the cytomegalovirus promoter. In one embodiment, the promoter is the cytomegalovirus promoter having the nucleic acid sequence set forth in SEQ ID NO. 5.

```
SEQ ID NO: 5: CMV promoter sequence
CTAGTTATTAATAGTAATCAATTACGGGGTCATTAGTTCATAGCCCAT

ATATGGAGTTCCGCGTTACATAACTTACGGTAAATGGCCCGCCTGGCT

GACCGCCCAACGACCCCCGCCCATTGACGTCAATAATGACGTATGTTC

CCATAGTAACGTCAATAGGGACTTTCCATTGACGTCAATGGGTGGAGT

ATTTACGGTAAACTGCCCACTTGGCAGTACATCAAGTGTATCATATGC

CAAGTACGCCCCCTATTGACGTCAATGACGGTAAATGGCCCGCCTGGC

ATTATGCCCAGTACATGACCTTATGGGACTTTCCTACTTGGCAGTACA

TCTACGTATTAGTCATCGCTATTACCATGGTGATGCGGTTTTGGCAGT

ACATCAATGGGCGTGGATAGCGGTTTGACTCACGGGGATTTCCAAGTC

TCCACCCCATTGACGTCAATGGGAGTTTGTTTTGCACCAAAATCAACG

GGACTTTCCAAAATGTCGTAACAACTCCGCCCCATTGACGCAAATGGG

CGGTAGGCGTGTACGGTGGGAGGTCTATATAAGCAGAGCTCGTTTAGT

GAACCGTCAGATCGCCTGGAGACGCCATCCACGCTGTTTTGACCTCCA

TAGAAGACACCGGGACCGATCCAGCCTCC
```

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. Preferably, the nucleic acid sequence PHB, is operably linked to a CMV promoter. In an embodiment, the CMV promoter has the nucleic acid sequence shown in SEQ ID 2. Other promoters and/or enhancers may be used, such as the CMV enhancer/chicken beta-actin promoter (also referred to as a "CAG promoter") (see, e.g., NIWA, et al., Gene, 108:193-199 (1991); DALY, et al., Proc. Natl. Acad. Sci. USA, 96:2296-2300 (1999); SONDHI, et al., Mol. Ther., 15:481-491 (2007)).

The vector may also include a termination sequence, such as for example, transcription termination is provided by the BGH (Bovine growth hormone) polyA, SV40 polyA, or TK (Thymidine kinase) polyA.

Nucleic acid vectors suitable for use in the present invention may be produced by any suitable method. In embodiments where the nucleic acid vector is a recombinant viral vector, delivery of the recombinant viral vector to a target tissue may be achieved by administration of viral particles (i.e., virions) containing the viral vector. For example, virions containing a recombinant AAV vector which carries a transgene (e.g., a PHB-coding sequence) may be produced by transfecting human embryonic kidney 293T cells with one of the transgene specific AAV vector plasmids and another plasmid containing the adenovirus helper and AAV rep and cap genes (specific to AAVrh.10, 8 or 9 as required). After 72 hours, the cells are harvested and virions are released from the cells by five freeze/thaw cycles. Subsequent centrifugation and benzonase treatment removes cellular debris and unencapsidated DNA. Iodixanol gradients and ion exchange columns may be used to further purify virions containing the AAV vector. Next, the purified virions are concentrated by a size exclusion centrifuge spin column to the required concentration. Finally, the buffer is exchanged to create the final vector products (virions containing the AAV vector which carries the transgene) formulated (for example) in 1× phosphate buffered saline. The viral titers may be measured by TaqMan® real-time PCR and the viral purity may be assessed by SDS-PAGE.

In some embodiments, virions containing a recombinant AAV vector are prepared based on procedures described by KANTOR et al. (Advances in Genetics, vol. 87, 2014, Chapter 2, "Clinical Applications Involving CNS Gene Transfer"); KAPLITT et al. (Lancet 369: 2097-105, 2007); WORGALL et al. (Human Gene Therapy 19:463-474 (2008); LEONE et al., Sci. Transl Med 4: 165ra163 (2012). In one embodiment, the AAV vector suitable for use in the present invention is produced according to the methods described in U.S. Pat. No. 6,342,390. In an alternate embodiment, the AAV vector suitable for use in the present invention is produced according to the methods described in U.S. Pat. No. 6,821,511.

Pharmaceutical Compositions and Delivery of the Gene Transfer Vector of the Present Invention.

The invention provides a composition containing the above-described gene transfer vector or viral particles comprising the gene transfer vector and a pharmaceutically acceptable (e.g. physiologically acceptable) carrier.

When the composition consists essentially of the instant gene transfer vector or virions and a pharmaceutically acceptable carrier, additional components can be included that do not materially affect the composition (e.g., adjuvants, buffers, stabilizers, anti-inflammatory agents, solubilizers, preservatives, etc.). When the composition consists of the gene transfer vector or virions and the pharmaceutically acceptable carrier, the composition does not comprise any additional components. Any suitable carrier can be used within the context of the invention, and such carriers are well known in the art. The choice of carrier will be determined, in part, by the particular site to which the composition may be administered and the particular method used to administer the composition. The composition optionally can be sterile with the exception of the gene transfer vector described herein. The composition can be frozen or lyophilized for storage and reconstituted in a suitable sterile carrier prior to use. The compositions can be generated in accordance with conventional techniques described in, e.g., Remington: The Science and Practice of Pharmacy, 21st Edition, Lippincott Williams & Wilkins, Philadelphia, Pa. (2001).

Suitable formulations for the composition include aqueous and non-aqueous solutions, isotonic sterile solutions, which can contain anti-oxidants, buffers, and bacteriostats, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the carrier is a buffered saline solution. More preferably, the gene transfer vector or virions is provided in a composition formulated to protect the gene transfer vector from damage prior to administration. For example, the composition can be formulated to reduce loss of the gene transfer vector on devices used to prepare, store, or administer the gene transfer vector or virions, such as glassware, syringes, or needles. The composition can be formulated to decrease the light sensitivity and/or temperature sensitivity of the gene transfer vector or virions. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the gene transfer vector or virions, facilitate administration, and increase the efficiency of the inventive method. Formulations for gene transfer vector-containing compositions are further described in, for example, WRIGHT, et al., Curr. Opin. Drug Discov. Devel., 6(2):174-178 (2003); WRIGHT, et al., Molecular Therapy, 12:171-178 (2005)).

The composition also can be formulated to enhance transduction efficiency. In addition, one of ordinary skill in the art will appreciate that the inventive gene transfer vector can be present in a composition with other therapeutic or biologically-active agents. For example, factors that control inflammation, such as ibuprofen or steroids, can be part of the composition to reduce swelling and inflammation associated with in vivo administration of the gene transfer vector or virions. Immune system stimulators or adjuvants, e.g., interleukins, lipopolysaccharide, and double-stranded RNA, can be administered to enhance or modify the response of PHB. Antibiotics, i.e., microbicides and fungicides, can be present to treat existing infection and/or reduce the risk of future infection, such as infection associated with gene transfer procedures.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

The composition can be administered in or on a device that allows controlled or sustained release, such as a sponge, biocompatible meshwork, mechanical reservoir, or mechanical implant. Implants (see, e.g., U.S. Pat. No. 5,443,505), devices (see, e.g., U.S. Pat. No. 4,863,457), such as an implantable device, e.g., a mechanical reservoir or an implant or a device comprised of a polymeric composition, are particularly useful for administration of the inventive gene transfer vector. The composition also can be administered in the form of sustained-release formulations (see, e.g., U.S. Pat. No. 5,378,475) comprising, for example, gel foam, hyaluronic acid, gelatin, chondroitin sulfate, a polyphosphoester, such as bis-2-hydroxyethyl-terephthalate (BHET), and/or a polylactic-glycolic acid.

Delivery of the compositions containing a gene transfer vector or virions disclosed herein may be intracerebral (including but not limited to intraparenchymal, intraventricular, or intracisternal), intrathecal (including but not limited to lumbar or cisterna magna), or any combination thereof.

Delivery may be by injection, or via a surgically implanted device. In certain embodiments, the delivery is targeted to specific regions of the brain. Examples of the specific regions of the brain include, but are not limited to, the hypothalamus, the hippocampus, the cerebellum, the temporal lobe of the cerebral cortex, the occipital lobe of the cerebral cortex, the parietal lobe of the cerebral cortex, and the frontal lobe of the cerebral cortex. Targeted delivery may be via injection, or, alternatively, by a surgically implanted device.

In one embodiment, a composition containing virions which include a gene transfer vector (e.g., an AAV vector carrying a PHB-coding sequence) disclosed herein is injected into the CA1 sector of the hippocampus.

In an alternate embodiment, the compositions containing virions which include a gene transfer vector (e.g., an AAV vector carrying a PHB-coding sequence) disclosed herein are delivered systemically, including but not limited to via intravenous injection.

In certain embodiments, the gene transfer vector expresses the exogenous prohibitin, once the vector is delivered into the subject's brain. In certain embodiments, the expression of the endogenous prohibitin is targeted to specific regions of the brain. Examples of the specific regions of the brain include, but are not limited to, the hypothalamus, the hippocampus, the cerebellum, the temporal lobe of the cerebral cortex, the occipital lobe of the cerebral cortex, the parietal lobe of the cerebral cortex, and the frontal lobe of the cerebral cortex.

In one embodiment, the exogenous prohibitin is expressed in the CA1 sector of the hippocampus.

In certain embodiments, expression of the exogenous prohibitin is targeted to a specific cell type. For example, in one embodiment, the expression of the exogenous prohibitin may be expressed in neuronal cells.

The dose of the gene transfer vector in the composition administered to the mammal will depend on a number of factors, including the size (mass) of the mammal, the extent of any side-effects, the particular route of administration, and the like. Preferably, the method of the present invention comprises administering a "therapeutically effective amount" of the composition comprising a gene transfer vector described herein. A "therapeutically effective amount" refers to an amount effective, at dosages and for periods of time necessary, to achieve a desired therapeutic result. The therapeutically effective amount may vary according to factors such as, age, sex, and weight of the individual, and the ability of the gene transfer vector to elicit a desired response in the individual. Generally speaking, the amount of an AAV vector required to achieve a particular therapeutic effect can be from about $0.5 \times 10^9$ viral particles per dose to about $2.5 \times 10^{12}$ viral particles per dose, or alternatively, per subject. Alternatively, the amount of an AAV vector in the composition required to achieve a particular therapeutic effect can be about $5 \times 10^{12}$ viral particles per kg to about $2 \times 10^{13}$ viral particles per kg, or to about $2 \times 10^{14}$ viral particles per kg body weight. Additional guidance for suitable dosages can also be found in, for example, KANTOR et al. (Advances n Genetics, vol. 87, 2014, Chapter 2, *"Clinical Applications Involving CNS Gene Transfer"*); KAPLITT et al. (Lancet 369: 2097-105, 2007); WORGALL et al. (Human Gene Therapy 19:463-474 (2008); LEONE et al., Sci. Transl Med 4: 165ra163 (2012). One of ordinary skill in the art can readily determine an appropriate gene transfer vector dose range to treat a patient having a particular disease or disorder, based on these and other factors that are well known in the art.

In a preferred embodiment of the invention, a gene transfer vector is administered (e.g., via AAV virions) once (a single dose) to the subject. It is believed that a single administration of the composition will result in persistent expression of the PHB expression in the subject with minimal side effects. However, in certain cases, it may be appropriate to administer the gene transfer vector multiple times (i.e., multiple doses) to ensure sufficient expression of the exogenous prohibitin. For example, the gene transfer vector may be administered to the mammal two or more times (e.g., 2, 3, 4, 5, 6, 6, 8, 9, or 10 or more times).

Expression of the exogenous prohibitin can be monitored in the subject's brain, by any suitable method readily selected by one of skill in the art. The monitoring can be 1 week post-administration of the gene transfer vector. Alternatively, the monitoring can be 2, 3, 4, 5, 6, 7, or 8, or more weeks post-administration of the gene transfer vector.

Neurological Disorders.

Neurological conditions include, for example, Alzheimer's Disease, Alexander disease, Alper's disease, Amyotrophic lateral sclerosis, Ataxia telangiectasia, Batten disease (also known as Spielmeyer-Vogt-Sjogren-Batten disease), Bovine spongiform encephalopathy (BSE), Canavan disease, Cockayne syndrome, Corticobasal degeneration, Creutzfeldt-Jakob disease, Huntington disease, HIV-associated dementia, Kennedy's disease, Krabbe disease, Lewy body dementia, Machado-Joseph disease (Spinocerebellar ataxia type 3), Multiple sclerosis, Multiple System Atrophy, Neuroborreliosis, Parkinson disease, Pelizaeus-Merzbacher Disease, mild cognitive impairment, frontotemporal dementia, traumatic brain injury, stroke, transient ischemic attack, dementia, prion disease, Pick's disease, corticobasal degeneration, Progressive supranuclear palsy; Dementia pugilistica (chronic traumatic encephalopathy); frontotemporal dementia and parkinsonism linked to chromosome 17; Lytico-Bodig disease; Tangle-predominant dementia; Ganglioglioma and gangliocytoma; Meningioangiomatosis; Subacute sclerosing panencephalitis; lead encephalopathy, tuberous sclerosis, Hallervorden-Spatz disease, lipofuscinosis. Argyrophilic grain disease; and Frontotemporal lobar degeneration. In one embodiment, the disease is Alzheimer's Disease.

The term "treat" or "treating" as used herein refers to accomplishing one or more of the following: (a) reducing the severity of the neurological disorder; (b) slowing or reversing the development of symptoms characteristic of the neurological disorder; (c) limiting worsening of symptoms characteristic of the neurological disorder; (d) limiting recurrence of the neurological disorder in subjects that have previously had the neurological disorder; and (e) limiting recurrence of symptoms in subjects that were previously symptomatic for the neurological disorder.

The neurological condition can result in of one or more of the following defects: cognitive defects in the subject, functional, biochemical or structural defects in the subject. Treatment according to the methods of the present invention may treat one, more than one, or all of the cognitive, functional, biochemical or structural defects in the subject.

A cognitive defect includes impairment in one or more of conditioned memory, spatial memory, contextual memory, memory retention, contextual learning, and conditioned learning.

Biochemical defects include, for example, tau hyperphosphorylation and accumulation of Aβ, or combinations thereof.

Amyloid Beta:

Aβ is derived from amyoid precursor protein (APP). APP is an integral membrane protein expressed in many tissues and concentrated in the synapses of neurons. The proteolytic cleavage of APP is a normal physiologic process. However, the amyloidogenic processing of APP has been linked to the presence of APP in lipid raft regions of cell membranes (EHEHALT, et al., J. Cell Biol., 160 (1):113-123 (2003)). Lipid rafts are membrane microdomains enriched in cholesterol, glycosphingolipids and glucosylphosphatidyl-inositol-(GPI)-tagged proteins implicated in signal transduction, protein trafficking and proteolysis. Within the lipid rafts it is believed that APP is cleaved first by the protease β-secretase (BACE) to generate the C-terminal intermediate fragment of APP, CAPPβ, which remains embedded in the membrane. CAPPβ subsequently is cleaved at a site residing within the lipid bilayer by γ-secretase. Aβ is released outside the cell, where it forms oligomers, resulting in neurotoxicity. The released Aβ may eventually accumulate, forming plaques.

In AD, amyloid plaques are dense, insoluble deposits of Aβ, the plaques may also contain fibrous structures formed from the microtubule-associated protein "tau". Aβ deposits can also lack the fibrous structures. Such deposits (diffuse plaques) have been observed in patients with dementia pugilistica.

Neurofibrillary Tangles:

During neurodegeneration, the microtubule-associated protein "tau" can be phosphorylated abnormally at proline directed serine/threonine phosphorylation sites, which can be detected using specific antisera. These serine/threonine (Ser/Thr) phoshorylation sites include Ser-202/Thr-205 (AT8 site), Ser-214 and/or Ser-214, Ser-181, and/or Ser-212 (AT100 site), Thr-231 and/or Ser-235 (TG3 site), and Ser-396/Ser-404 (PHF-1 site). Neurofibrillary tangles (NFTs) are aggregates of tau, which have become hyperphosphorylated and accumulate inside neurons. For example, neurons in the brain regions typically affected in Alzheimer's disease (AD) including, but not limited to, entorrhinal cortex, hippocampus, parahippocampus gyms, amygdale, frontal, temporal, parietal and occipital association cortices, and certain subcortical nuclei projecting to these regions) contain large, nonmembrane-bound bundles of abnormal fibers that occupy much of the perinuclear cytoplasm.

NFTs are not specific for AD. NFTs appear in multiple brain diseases, and may contribute to neurodegeneration in more than one disease state. NFTs are also found in some frontotemporal dementias, myotonic dystrophy, viral panencephalitis, dementia pugilistica, some prion diseases, and other brain diseases, including Creutzfeldt-Jakob disease, Supranuclear Palsy, corticobasal neurodegeneration and Frontaltemporal Dementia with Parkinsonism linked to chromosome 17 (FTDP-17).

Structural defects include amyloid plaques, diffuse amyloid plaques, neurofibrillary tangles, neuronal loss, synaptic loss, or any combination thereof.

Functional defects include impairment in long-term potentiation of neurons.

The effectiveness of the compositions and methods of the present invention can be assayed by a variety of protocols. For example, the effects of the compositions and methods of the present invention on spatial memory can be determined using the methods disclosed in PARK et al.

The effects of the compositions and methods of the present invention in human subjects can be determined by methods routine to those of skill in the art.

One of skill in the art also can directly measure amyloid peptide accumulation levels, neurofibrillary tangle formation and neurodegeneration in animal models. Furthermore, amyloid peptide may be measured in a sample of a subject's cerebrospinal fluid.

Methods of assaying amyloid peptide include ELISA. Such methods are well known by those of ordinary skill in the art.

Methods of assaying tau hyperphosphoryation include ELISA using antibodies specific for serine/threonine (Ser/Thr) phoshorylation sites including Ser-202/Thr-205, Ser-214 and/or Ser-214, Ser-181, and/or Ser-212, Thr-231 and/or Ser-235, and Ser-396/Ser-404 (PHF-1 site). Such methods are well known by those of ordinary skill in the art.

Methods of assaying long-term potentiation in neurons include electrophysiology assays, such as the assays disclosed in MA, et al., J Neurosci, 31(15):5589-5595 (2011).

Subjects.

The subject suitable for treatment according to the methods of the present invention may be any animal, including a human and non-human animal that has a neurological disorder.

In one embodiment, the subject has been clinically diagnosed with a neurological disorder.

In one embodiment, the subject has one or more of the following defects: cognitive defects, functional, biochemical or structural defects. A cognitive defect includes impairment in one or more of conditioned memory, spatial memory, contextual memory, memory retention, contextual learning, and conditioned learning. Biochemical defects include, for example, tau hyperphosphorylation and accumulation of Aβ, or combinations thereof. Structural defects include amyloid plaques, diffuse amyloid plaques, neurofibrillary tangles, neuronal loss, synaptic loss, or any combination thereof. Functional defects include impairment in long-term potentiation of neurons. In some embodiments, the subject is generally diagnosed with the condition of the subject invention by skilled artisans, such as a medical practitioner.

Non-human animals includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses. The subject may also be livestock such as, cattle, swine, sheep, poultry, and horses, or pets, such as dogs and cats.

The methods of the invention described herein can be employed for subjects of any species, gender, age, ethnic population, or genotype. Accordingly, the term subject includes males and females, and it includes elderly, elderly-to-adult transition age subjects adults, adult-to-pre-adult transition age subjects, and pre-adults, including adolescents, children, and infants.

Examples of human ethnic populations include Caucasians, Asians, Hispanics, Africans, African Americans, Native Americans, Semites, and Pacific Islanders. The methods of the invention may be more appropriate for some ethnic populations such as Caucasians, especially northern European populations, as well as Asian populations.

The term subject also includes subjects of any genotype or phenotype as long as they are in need of the invention, as described above. In addition, the subject can have the genotype or phenotype for any hair color, eye color, skin color or any combination thereof. The term subject includes a subject of any body height, body weight, or any organ or body part size or shape.

The present description is further illustrated by the following examples, which should not be construed as limiting in any way. The contents of all cited references (including literature references, issued patents, and published patent applications as cited throughout this application) are hereby expressly incorporated by reference.

EXAMPLES

Example 1

PHB is a Potent Modulator of Mitochondrial ROS Production

PHB overexpression has been shown to attenuate ROS production from complex I in cultured primary mouse cortical neurons. Neurons dissected at E16 and maintained for 5 days in vitro were co-transfected with two plasmids encoding human PHB and GFP, respectively. 5 days after transfection, neurons were challenged with the specific mitochondrial respiratory chain complex I inhibitor Rotenone (5 μM). Neurons co-transfected with empty vector and GFP served as controls. PHB expressing neurons exhibited reduced rotenone-induced mitochondrial ROS production, assessed by the mitochondrial ROS reporter MitoSOX (ZHOU, et al., J Neurosci, 32(2):583-592 (2012)). Down-regulation of endogenous prohibitin by siRNA enhanced ROS production in primary neurons treated with glutamate (25 mM for 5 hrs) (ZHOU, et al., J Neurosci, 32(2):583-592 (2012)). These data obtained in cultured neurons indicated that prohibitin overexpression is a viable strategy to dampen mitochondrial ROS production in models of neuronal injury in vitro. The effects of prohibitin expression in vivo were tested in the subsequent studies.

Example 2

PHB Expression in Hippocampal Tissue Suppresses Post-Ischemic ROS Production

Viral particles containing a recombinant AAV vector coding for human PHB sequence (See FIG. 1) were injected stereotactically into the CA1 sector of the hippocampus of 12 month-old APP-Tg mice. For simplicity, injections of virions containing AAV vectors in this and following examples are also referred to in this and the following examples as injections of AAV vectors.

The AAV vector encoded in a 5' to 3' direction, an inverted terminal repeat (ITR) sequence; a cytomegalovirus (CMV) promoter sequence, a prohibitin (PHB) sequence, an internal ribosome entry site (IRES) sequence, an enhanced green fluorescent protein (EGFP) sequence, and a bovine growth hormone polyadenylation (BGH-pA) sequence. The nucleic acid sequence for the prohibitin used for this study is set forth in SEQ ID NO: 1.

Under isoflurane anesthesia (1.5% to 2.0%), a midline skin incision was made between the bregma and interaural line. A 2 mm hole was drilled in the skull and AAV-PHB or AAV-control virus in 2 μl Ringer solution (titer: 1012-1013 genomic copy/ml) was injected into CA1, using a glass micropipette. The stereotaxic coordinates were 1.8 mm posterior to bregma, 1.7 mm lateral to the midline and 1.3 mm below the dura. The solution was slowly injected over 60 min and the needle was left in place for an additional 10 min. The needle was then slowly withdrawn and the incision closed. AAV-injected mice were later used for experiments.

Figure 2:
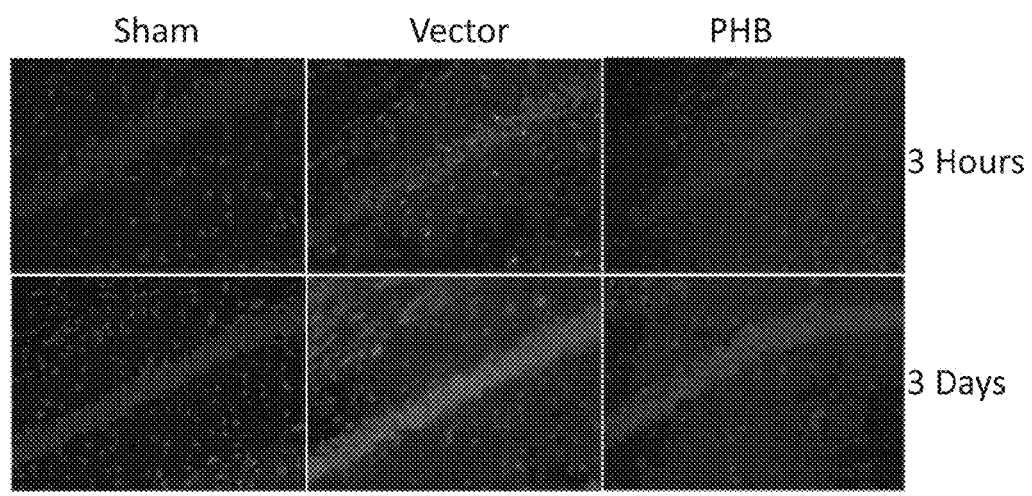
FIG. 2 (A) shows post-ischemic ROS production in hippocampus assessed by DHE staining in CA1 region. Two peaks of ROS were found after BCCAO at 3 hrs and 3 days of reperfusion. PHB expression suppressed both peaks of ROS production.
Figure 2:
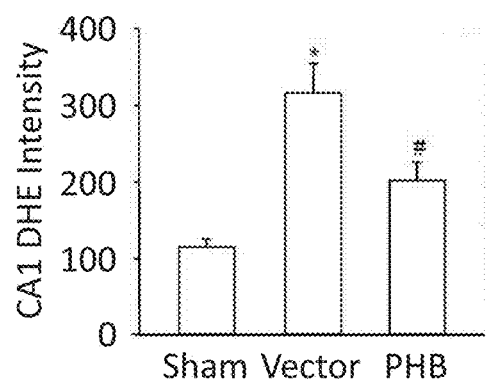
Figure 2:
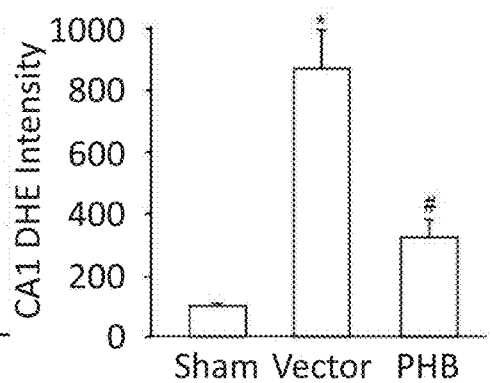

Three weeks after AAV vector injection, transient forebrain ischemia produced by bilateral common carotid artery occlusion (BCCAO) was induced in the mice. We observed a biphasic increase in ROS in the CA1 region of the hippocampus 3 hours and 3 days after, a procedure (BCCAO) that mimics cardiac arrest in human patients. PHB expression by AAV-mediated delivery in hippocampus three weeks prior to this procedure significantly attenuated ROS production at both time points, as illustrated in FIG. 2, which shows the effect of PHB expression on ROS production in the hippocampus of mice treated using the methods of the present invention. AAV mediated PHB expression in mouse hippocampus suppressed post-ischemic ROS production. AAV-PHB and AAV control were injected in CA1 region of mouse hippocampus. Surgeries were performed on the injected mice to produce transient global ischemia by bilateral carotid common artery occlusion (BCCAO). FIG. 2 (A) shows the post-ischemic ROS production in hippocampus assessed by DHE staining in CA1 region. Two peaks of ROS were found after BCCAO at 3 hrs and 3 days of reperfusion.

PHB expression suppressed both peaks of ROS production. FIG. 2 (B) and (C) shows the quantitative analysis of DHE fluorescence in the two peaks. PHB expression reduced the ROS signal in hippocampus at 3 hrs and at 3 days. *$p<0.05$ compared to sham group; #$p<0.05$, compared to vector group by one way ANOVA analysis followed by Dunnett's test, n=5/group.

Since mitochondria are a major source of post ischemic ROS production, the PHB expression mediated ROS attenuation in stroke indicates it likely will be an effective modulator for oxidative stress in AD brain as well.

Example 3

AAV-Mediated PHB Expression in CA1 Protects Against BCCAO-Induced Cell Death

Figure 3:
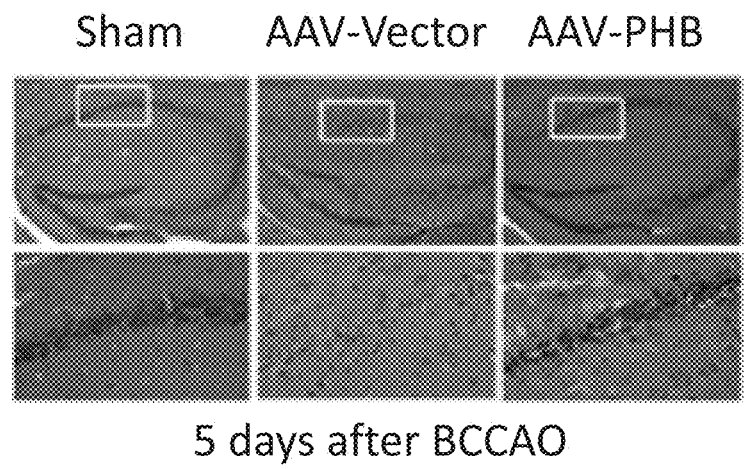
FIG. 3 (A) shows H & E staining of hippocampal sections 5 days after BCCAO.
Figure 3:
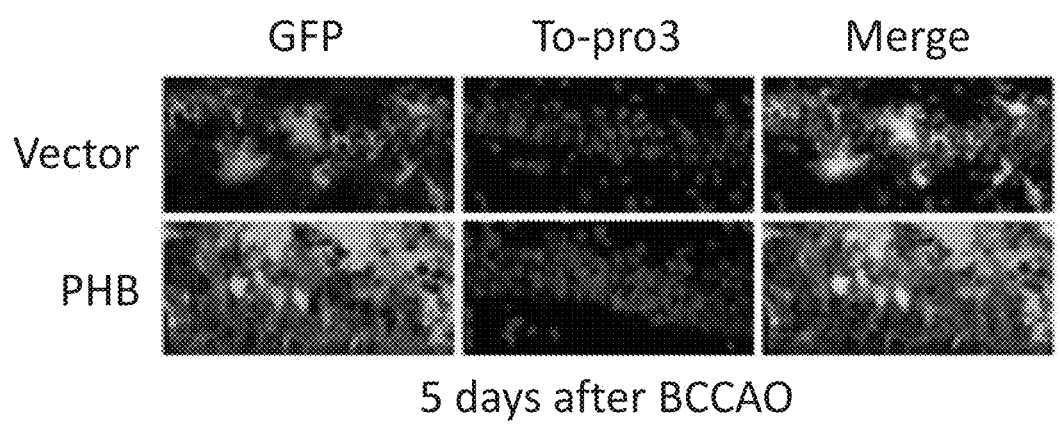
Figure 3:
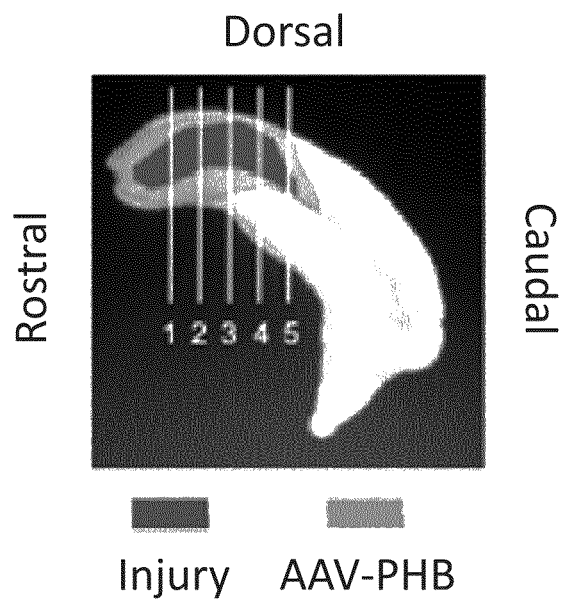
Figure 3:
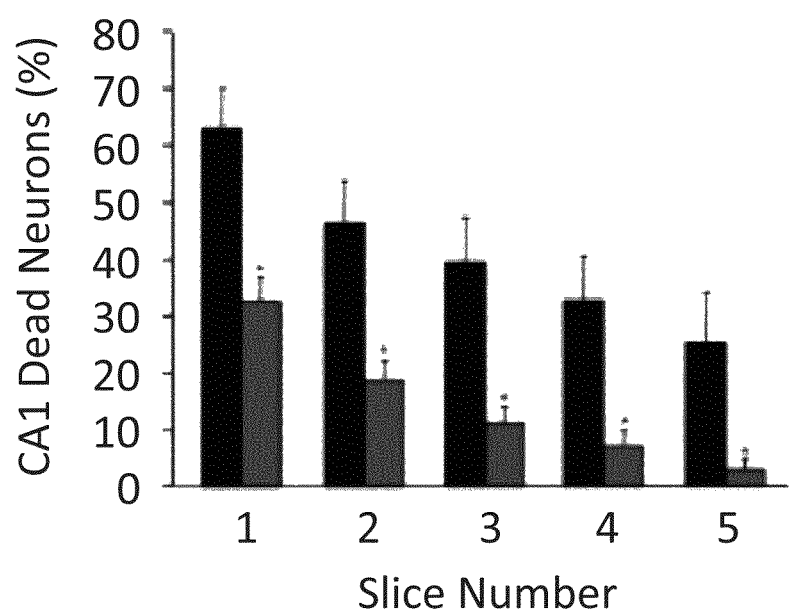

Bilateral carotid common artery occlusion (BCCAO) caused extensive neuronal death in the CA1 region of mice injected with control vector, assessed by morphological criteria. In mice that received AAV-PHB injections, neuronal death in the CA1 region was prevented (see FIG. 3, showing the effect of PHB expression following treatment according to the methods of the present invention on cell death following BCCAO). FIG. 3 (A) shows H & E staining of hippocampal sections 5 days after BCCAO. AAV-vector injected hippocampus suffered extensive cell death in CA1 (middle panels), an effect reduced by PHB expression (right panels). FIG. 3 (B) shows cell morphology in hippocampus 5 days after BCCAO. Hippocampal sections were stained with Alexa 488 conjugated anti-GFP antibody and counterstained with the nuclear dye To-pro-3. Top panels, vector injected. Lower panels PHB injected. Note that many of the surviving cells express PHB.

3D reconstruction from serial sections demonstrated that the ischemic lesion was located entirely within the volume of the tissue expressing PHB (see FIG. 3(C)). FIG. 3 (C) depicts a diagram illustrating the location of cell injury after BCCAO in a 3D reconstruction of the hippocampus (red). The green area marks the extent of PHB gene transfer. Note that the area of injury is comprised within the area of PHB gene transfer. Lines indicate the 5 levels at which cell counts were obtained. A reduction in cell death was observed at all rostrocaudal levels, although the protection was more pronounced caudally, where the injury was less severe (see FIG. 3(D)). FIG. 3 (D) shows that PHB gene transfer reduces cell death at all levels of the lesion indicated in C. *$p<0.05$ in each section, n=15 mice for vector and 20 for PHB. Collectively, these results demonstrate that AAV-PHB gene transfer protects CA1 cells from the deleterious effects of transient forebrain ischemia.

Example 4

AAV-Mediated PHB Gene Transfer in the Hippocampal Tissue of Mice Expressing Human APP Containing the Swedish Mutation (Tg2576 Mice, Herein Defined as APP-Tg)

Figure 4:
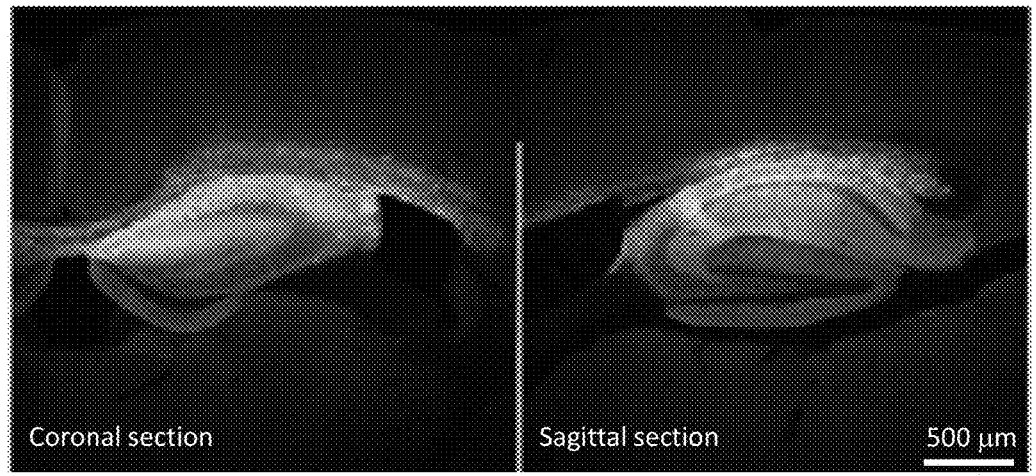
FIGS. 4 (A) to 4 (C) show the effect of PHB expression on gene expression in hippocampus of 12 month old APP-Tg mouse.
Figure 4:
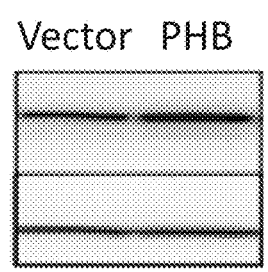
Figure 4:
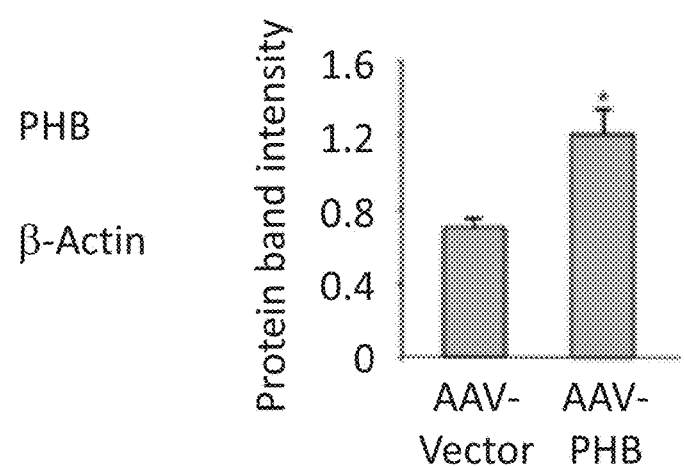

We injected an AAV vector (as described in Example 2) in which GFP was under the control of CMV promoter (in serotype AAV 2, which favored neuronal expression in our screening test) expressing either GFP control (AAV-GFP) or PHB under the control of the CMV promoter, in the hippocampus of 12 month old mice and demonstrated that AAV mediated gene transfer is capable of delivering PHB in APP-Tg mice. Examination of brain sections showed that GFP expression was extensive in the entire CA1 region. FIG. 4 (A) shows brain sections were prepared 3 weeks post procedure to assess the level and location of GFP expression. Slices were counterstained with neuronal marker MAP-2 (red) to aid the viewing of GFP. FIG. 4(A) demonstrated that that gene delivery by AAV-2 resulted in transduction of a large number of cells in the hippocampus. FIG. 4 (B) shows western blots, showing PHB protein levels in hippocampal tissue injected with AAV-GFP (vector) and AAV-PHB (PHB). FIG. 4 (C) is a quantitation of the protein band in FIG. 4 (B). *$p<0.05$, n=3. Hippocampal PHB levels resulting from AAV-PHB injection was 48% higher than in control injected tissue, by western blot analyses (n=3, $p<0.05$. See FIG. 4(B) and (C)). These results demonstrate that AAV-PHB can be delivered and expressed in hippocampus of symptomatic APP-Tg mice, at a time when Aβ plaques are already abundant (PARK, et al., Proc Natl Acad Sci USA, 105 (4):1347-1352 (2008)), a key milestone, in our proposed study.

Example 5

AAV Mediated PHB Gene Transfer Restores the Impairments of LTP and Cognitive Functions in APP-Tg Mice 400 μm hippocampal slices of excised brain tissue from 12-month old APP-Tg mice having undergone AAV injection (as described in Example 2) were prepared using a vibratome, as described previously (MA, et al., J Neurosci, 31(15):5589-5595 (2011)). The slices were maintained at room temperature in a submersion chamber with artificial cerebrospinal fluid (ACSF) containing 125 mM NaCl, 2.5 mM KCl, 2 mM $CaCl_2$, 1 mM $MgCl_2$, 1.25 mM $NaH_2PO_4$, 24 mM $NaHCO_3$, and 15 mM glucose, bubbled with 95% $O_2$/5% $CO_2$. Slices are incubated for at least 2 hours before the experiments and the operator is blinded to the treatment groups. For LTP electrophysiology experiments, slices were transferred to recording chambers (preheated to 32° C.), where they were superfused with oxygenated ACSF. Monophasic, constant-current stimuli (100 μsec) were delivered with a bipolar silver electrode placed in the stratum radiatum of area CA3, and the field excitatory postsynaptic potentials (fEPSPs) were recorded in the stratum radiatum of area CA1 with electrodes filled with ACSF (Re=2-4MΩ). Baseline fEPSPs were monitored by delivering stimuli at 0.033 Hz. fEPSPs were acquired, and amplitudes and maximum initial slopes measured, using pClamp 10 (Axon Instruments, Foster City, Calif.). LTP was induced with a high-frequency stimulation (HFS) protocol consisting of two 1-second long 100 Hz trains, separated by 60 seconds, delivered at 70-80% of the intensity that evoked spiked fEPSPs.

Figure 5:
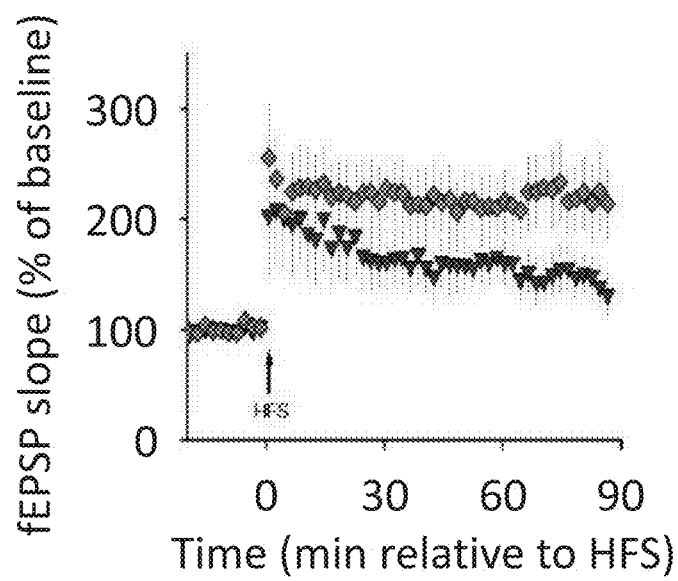
FIGS. 5 (A) to 5 (C) show the effect of PHB expression on LTP impairment in hippocampal slices of APP-Tg mice. AAV mediated PHB gene transfer rescues the LTP impairment in hippocampal slices of APP-Tg mice. AAV-vector (inverted triangles) or AAV-PHB (diamonds) were injected into either 12 month old APP-Tg mice (FIG. 5 (A)) or WT control (FIG. 5 (B), (squares and circles, respectively)).
Figure 5:
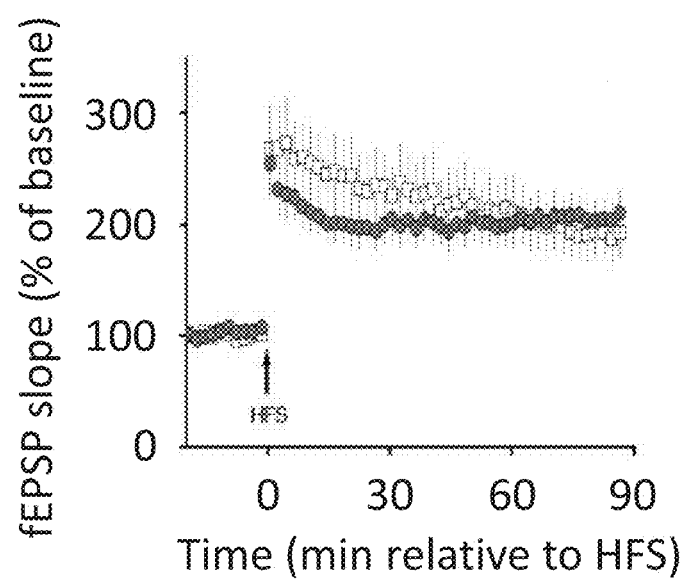
Figure 5:
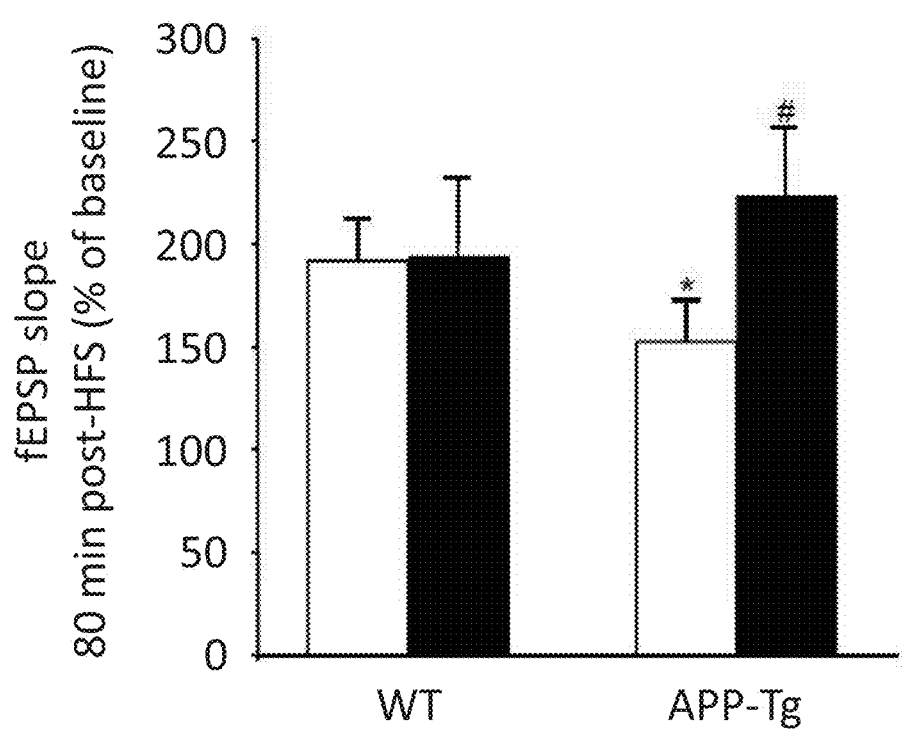

FIG. 5 shows the effect of PHB expression following treatment according to the methods of the present invention on LTP impairment in hippocampal slices of APP-Tg mice. AAV mediated PHB gene transfer rescues the LTP impairment in hippocampal slices of APP-Tg mice. AAV-vector or AAV-PHB were injected into either 12 month old APP-Tg mice (A) or WT control (B).

It is well-established that 12-month old APP-Tg mice have impaired hippocampal long-term potentiation (LTP) (Ma and Klann 2012), due to loss of synaptic plasticity. We observed that PHB expression by AAV-mediated gene transfer rescued the impairment in LTP, as illustrated in FIG. 5 (A), while PHB expression did not affect LTP in WT mice (FIG. 5 (B)). FIG. 5 (A) demonstrated that hippocampal LTP was impaired in APP-Tg mice and the impairment was rescued by AAV-PHB gene transfer. FIG. 5 (B) demonstrated that hippocampal LTP was maintained in slices from WT mice. PHB did not alternate the LTP in WT slice. FIG. 5(C) shows cumulative data showing mean fEPSP slopes 80 minutes post-HFS based on the LTP experiments in panel A and B, *p<0.05 compared to WT; #p<0.05 compared to APP-Tg with vector injection, n=4-6 samples/group.

Example 6

AAV Mediated PHB Gene Transfer Restores the Impairments of Cognitive Functions in APP-Tg Mice (1) Y-Maze:

Spatial working memory in mice were evaluated by the Y-maze test, as previously described (PARK, et al., Proc Natl Acad Sci USA, 110(8):3089-3094 (2013); PARK, et al., Proc Natl Acad Sci USA, 105 (4):1347-1352 (2008)). The operator was blinded to the AAV species the mice had received. The maze was made of three arms converging at equal angles. Arm dimensions are 40 cm in length, 13 cm in height, and 3 and 10 cm in width at the bottom and top, respectively. Each mouse was placed at the end of one arm and allowed to freely explore the apparatus for 8 minutes. The sequence and number of all arm entries were recorded for each animal throughout the test. Alternation rate was defined as entries into all three arms on consecutive occasions using the following formula: Alternation rate (%)=Number of alternations/(Number of total arm entries−2)×100. Trials in which the number of total arm entries is less than 10 were excluded from the analysis.

(2) Objection Recognition:

This test takes advantage of rodent's tendency to approach and explore novel objects. The recognition of the "familiar" object that leads to discrimination between the novel object and the "familiar" object requires the intact memory of previously experienced object (DERE, et al., Neuroscience & Biobehavioral Reviews, 31(5):673-704 (2007)). The test did not require preliminary training and no stress was imposed to force the animal to learn. The test was performed as previously described (BEVINS, et al., Nat Protoc, 1(3):1306-1311 (2006)). Briefly, the mouse was placed into an opaque rectangular plastic box measuring 25×30×15 (height) cm in which two identical objects were placed on two corners. After a 5 min period to allow the mouse to familiarize with the objects, the animal was removed from the box and returned to its home cage for 1 hr. After exchanging one object with a novel object with different color and shape, the mouse was put back in the box and allowed to explore for 3 min under video recording. The video was analyzed for time spent exploring the novel object. The contact time was defined as the time exploring the object with nose, mouth, and paws. The results were reported as a difference score (novel object interaction time−familiar object interaction time).

Figure 6:
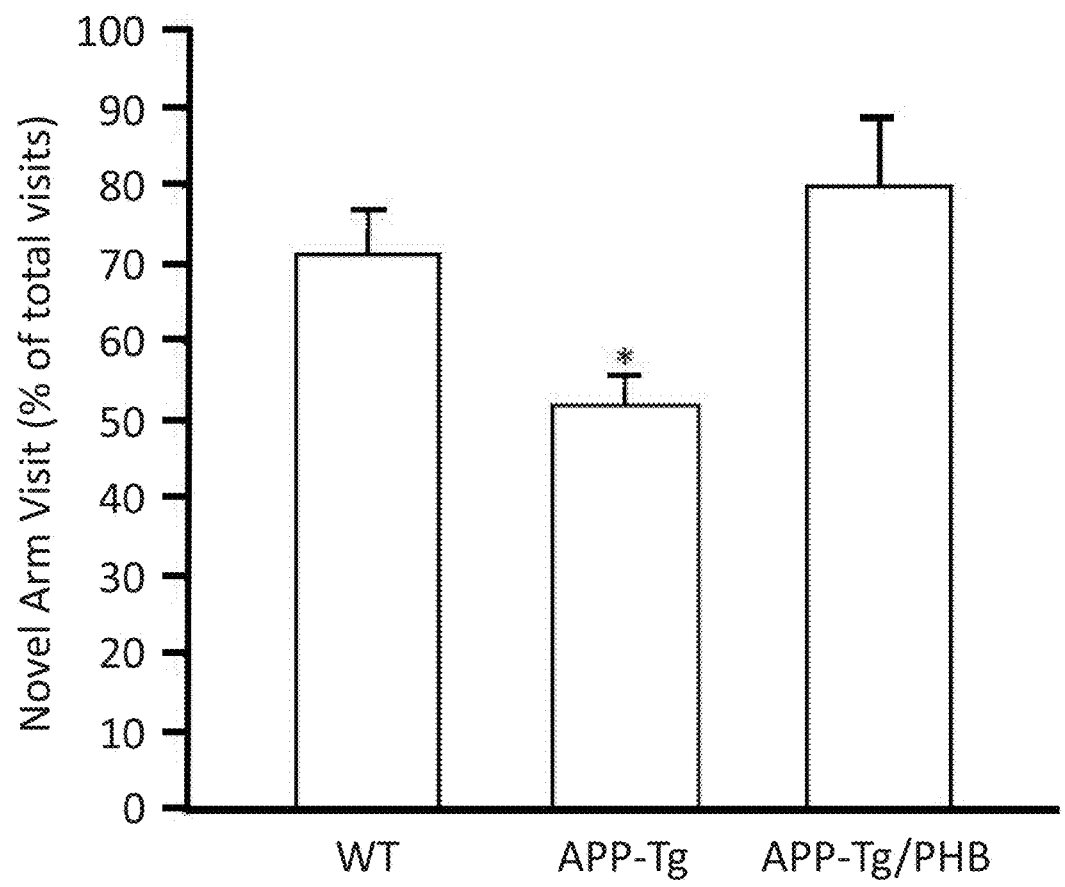
FIG. 6 shows the effect of PHB expression on spatial memory loss.

Untreated 12-month old APP-Tg mice showed reduced novel arm visits in the Y-maze test, indicative of deteriorated cognitive functions (PARK, et al., Proc Natl Acad Sci USA, 105 (4):1347-1352 (2008)). In agreement with the LTP rescue, cognitive deterioration in APP-Tg mice was completely rescued by PHB expression. FIG. 6 shows the effect of PHB expression following treatment according to the methods of the present invention on spatial memory loss. AAV mediated PHB gene transfer restored spatial memory loss in old APP-Tg mice. Y-maze arm alteration test for AAV-PHB and AAV-vector injected 12 month old APP-Tg mice compared to age matched WT controls. PHB expression restored the decrease in novel arm visits in APP-Tg mice. *p<0.05, n=4-6/group.

Example 7

Determination of Aβ Load

Aβ load is determined in hippocampus tissue as described previously (Park et al. 2008). Briefly, the tissue of AAP-Tg and WT controls injected with AV-PHB or AAV-vector is post-fixed in 4% PFA. Coronal sections (20 μM thick) are cut in a cryostat at 100-μm intervals and processed for immunocytochemistry using an Aβ antibody (4G8; Sigma). Gray scale images (magnification: ×1) of hippocampus are digitized with a camera (Q Imaging; Barnaby). The number of plaques per square millimeter is manually counted in the hippocampus. The Aβ load is determined in a blinded manner from the area occupied by the plaques relative to the total area of hippocampus, using NIH Image J software. The mice treated with PHB display hindrance of Aβ reuptake into neurons. Aβ total amount remains the same, however Aβ load in neurons is reduced. Aβ load in normal neurons is approximately 3.5 mm$^2$, and PHB treatment reduces Aβ load by about 45%.

Although the various aspects of the invention have been illustrated above by reference to examples and preferred embodiments, it will be appreciated that the scope of the invention is defined not by the foregoing description but by the following claims properly construed under principles of patent law.

What is claimed is:

1. A method comprising administering to a subject having Alzheimer's disease with impaired long-term potentiation, a gene transfer vector comprising a nucleic acid sequence encoding an exogenous prohibitin, wherein said gene transfer vector is administered to said subject by injection to the hippocampus, and wherein said gene transfer vector expresses the exogenous prohibitin in the hippocampus of the subject, thereby treating said Alzheimer's disease with impaired long-term potentiation.

2. The method of claim 1, wherein the subject further shows a cognitive defect selected from the group consisting of impairments in conditioned memory, impairments in spatial memory, impairments in contextual memory, impairments in memory retention, impairments in contextual learning, and impairments in conditioned learning.

3. The method of claim 1, wherein the subject further shows a biochemical defect selected from the group consisting of tau hyperphosphorylation, and accumulation of amyloid beta (Aβ).

4. The method of claim 1, wherein the subject further shows a structural defect selected from the group consisting of amyloid plaques, diffuse amyloid plaques, neurofibrillary tangles, neuronal loss, and synaptic loss.

5. The method of claim 1, wherein the gene transfer vector is an adeno-associated virus (AAV) nucleic acid vector, which encodes, in a 5' to 3' direction:

a. a first adeno-associated viral inverted terminal repeat (ITR), b. a promoter controlling the expression of a nucleic acid sequence encoding an exogenous prohibitin, c. a nucleic acid encoding an exogenous prohibitin, and d. a second adeno-associated viral ITR.

6. The method of claim 5, wherein the AAV nucleic acid vector is administered to the subject in a single dose.

7. The method of claim 5, wherein the AAV nucleic acid vector is administered to the subject in multiple doses.

8. The method of claim 5, wherein the AAV nucleic acid vector is administered via injection into the CAI region of the hippocampus.

9. The method of claim 1, wherein the exogenous prohibitin is encoded by the nucleic acid sequence set forth in SEQ ID NO: 1.

10. The method of claim 1, wherein the exogenous prohibitin is encoded by the nucleic acid sequence set forth in SEQ ID NO: 2.

11. The method according to any one of claims 5-7 and 8, wherein administration of the AAV nucleic acid vector is achieved by virions comprising said AAV nucleic acid vector.

* * * * *